(12) United States Patent
Su et al.

(10) Patent No.: US 11,566,293 B2
(45) Date of Patent: Jan. 31, 2023

(54) DNA METHYLATION BIOMARKERS FOR BLADDER CANCER

(71) Applicant: University of Southern California, Los Angeles, CA (US)

(72) Inventors: Sheng-Fang Su, Los Angeles, CA (US); Gangning Liang, Los Angeles, CA (US); Peter Jones, Los Angeles, CA (US); Kimberly Siegmund, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/799,559

(22) Filed: Feb. 24, 2020

(65) Prior Publication Data
US 2020/0347459 A1 Nov. 5, 2020

Related U.S. Application Data

(62) Division of application No. 14/890,424, filed as application No. PCT/US2014/037591 on May 9, 2014, now Pat. No. 10,570,455.
(Continued)

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01); *C12Q 2600/158* (2013.01)

(58) Field of Classification Search
CPC ............ C12Q 1/6886; C12Q 2600/118; C12Q 2600/154; C12Q 2600/158
See application file for complete search history.

(56) References Cited

U.S. PATENT DOCUMENTS

| | | |
|---|---|---|
| 2009/0054260 A1 | 2/2009 | Sidransky |
| 2011/0028333 A1 | 2/2011 | Christensen et al. |

(Continued)

FOREIGN PATENT DOCUMENTS

| | | |
|---|---|---|
| WO | 2008/009365 A2 | 1/2008 |
| WO | 2010/149782 A1 | 12/2010 |

(Continued)

OTHER PUBLICATIONS

Feng et al. PNAS. 2010. 107(19):8689-8694. (Year: 2010).*
(Continued)

*Primary Examiner* — Joseph G. Dauner
(74) *Attorney, Agent, or Firm* — DLA Piper LLP (US)

(57) ABSTRACT

A method for the prediction, prognosis and/or diagnosis of bladder cancer or bladder cancer recurrence in a subject, the method includes: providing a test sample from the subject; measuring DNA methylation levels of at least a portion of two or more polynucleotides selected from the group consisting of HOXA9, SOX1, NPY, IRAK3, L1-MET, and ZO2 in the test sample; calculating a risk score based on the measured DNA methylation levels, comparing the calculated risk score to a cut-off value derived from a reference DNA methylation profile based on DNA methylation levels of the one or more biomarkers derived from a control group, members of which had bladder cancer; and based on the comparison calculated risk score to the cut-off value, determining at least one of: (1) whether bladder cancer has recurred; (2) whether there is likelihood that the bladder cancer will recur; and (3) whether the patient has bladder cancer.

6 Claims, 10 Drawing Sheets

Specification includes a Sequence Listing.

Related U.S. Application Data

(60) Provisional application No. 61/821,838, filed on May 10, 2013.

(56) References Cited

U.S. PATENT DOCUMENTS

2012/0053083 A1  3/2012  Daemen et al.
2012/0252020 A1  10/2012  Shuber

FOREIGN PATENT DOCUMENTS

WO  2013/022995 A2  2/2013
WO  2014/020124 A1  2/2014

OTHER PUBLICATIONS

Shames et al. PLoS Medicine. 2006. 3(12):e486. (Year: 2006).*
Walter et al. Clin Cancer Res. 2012. 18(8):2360-2373. (Year: 2012).*
Chihara et al., "Diagnostic markers of urothelial cancer based on DNA methylation analysis," BMC Cancer, vol. 13, No. 275. Jun. 4, 2013, pp. 1-10.
European Search Report and Search Opinion Received for EP Application No. 14795476.2, dated Dec. 12, 2016, 9 pages.
Han et al., "Epigenetic Alterations in Bladder Cancer and Their Potential Clinical Implications", Advances in Urology, vol. 2012, Article ID 546917, Jan. 1, 2012, 11 pages.
International Preliminary Report on Patentability, received for PCT Patent Application No. PCT/US2014/037591, dated Nov. 10, 2015, 9 pages.
International Search Report and Written Opinion received for PCT Patent Application No. PCT/US14/037591, dated Oct. 14, 2014, 10 pages.
Reinert et al., "Comprehensive Genome Methylation Analysis in Bladder Cancer: Identification and Validation of Novel Methylated Genes and Application of These as Urinary Tumor Markers", Clinical Cancer Research, vol. 17, No. 17, Sep. 1, 2011, pp. 5582-5592.
Reinert et al., "Diagnosis of Bladder Cancer Recurrence Based on Urinary Levels of EOMES, HOXA9, POU4F2, TWIST1, VIM, and ZNF154 Hypermethylation", PLOS One, vol. 7, No. 10, Oct. 2012, e46297, 9 pages.
Su et al., "A Panel of Three Markers Hyper- and Hypomethylated in Urine Sediments Accurately Predicts Bladder Cancer Recurrence," Clinical Cancer Research, vol. 20, No. 7, Apr. 1, 2014, pp. 1978-1989.
Wolff et al., "Hypomethylation of a LINE-1 Promoter Activates an Alternate Transcript of the MET Oncogene in Bladders with Cancer", PloS Genetics, vol. 6, No. 4, 2010, e1000917, 13 pages.
Wolff et al., "Unique DNA Methylation Patterns Distinguish Non-invasive and Invasive Urothelial Cancers and Establish an Epigenetic Field Defect in Premalignant Tissue", Cancer Research, vol. 70, No. 20, 2010, pp. 8169-8178.
Wolff et al., "Unique DNA Methylation Patterns Distinguish Non-invasive and Invasive Urothelial Cancers and Establish an Epigenetic Field Defect in Premalignant Tissue", Cancer Research, vol. 70, No. 20, Sep. 14, 2010, pp. 8169-8178.

* cited by examiner

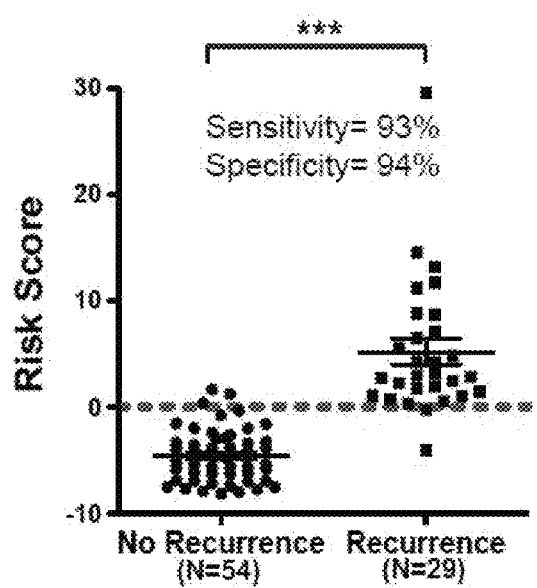
FIG. 2A
FIG. 2B
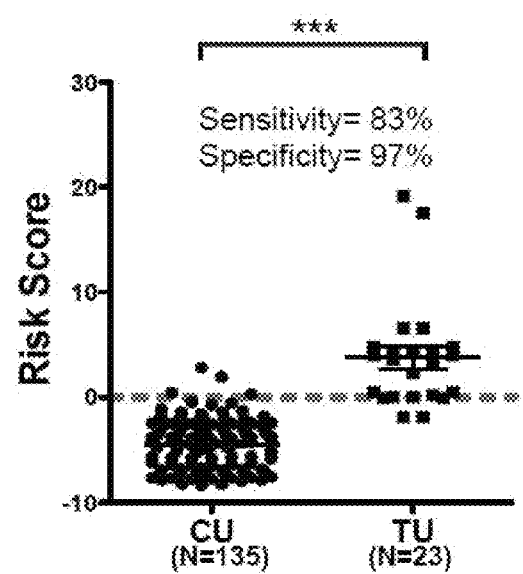
FIG. 2C

SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
atgaaatttg tagttttata atttt                                    25

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
attacccaaa accccaataa taac                                     24

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 3
gttttataat ttt                                                 13

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 4
ggtatttggg attagtatat gtttag                                   26

```
<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
ctatctcctt cctcctac                                                    18

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
ttagtatatg tttag                                                       15

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7
gggttgtttt tattttggt aggattaga                                         29

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
caccaaaacc caaatatcta                                                  20

<210> SEQ ID NO 9
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 9
aggaaagtag ggat                                                        14

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
ggagttttga gttttgggtt tt                                               22

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide
```

<400> SEQUENCE: 11
cctaaccaaa cctaaaaatt acc            23

<210> SEQ ID NO 12
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 12
aggtgtgaag ggg            13

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
ggtttttaga taggatttaa aattttgag            29

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
caaaacctca cacaaacaac ttc            23

<210> SEQ ID NO 15
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 15
aggttttttt agtt            14

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gtgtttttta agtgaggtaa tgtt            24

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
atccaaccac tacaaactac            20

<210> SEQ ID NO 18
<211> LENGTH: 16

```
<212> TYPE: DNA
<213> ORGANISM: Artificial Sequence
<220> FEATURE:
<223> OTHER INFORMATION: Synthetic oligonucleotide

<400> SEQUENCE: 18
gttgggagtt gtagat                                                  16
```

DNA METHYLATION BIOMARKERS FOR BLADDER CANCER

CROSS-REFERENCE TO RELATED APPLICATIONS

This application is a divisional application of U.S. application Ser. No. 14/890,424 filed Nov. 10, 2015, now issued as U.S. Pat. No. 10,570,455, which is a 35 USC § 371 National Stage application of International Application No. PCT/US2014/037591 filed May 9, 2014, now expired; which claims the benefit under 35 USC § 119(e) to U.S. Application Ser. No. 61/821,838 filed May 10, 2013. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under R01 CA083867, and R01 CA124518 awarded by the National Institutes of Health. The government has certain rights in the invention.

INCORPORATION BY REFERENCE OF SEQUENCE LISTING

The material in the accompanying sequence listing is hereby incorporated by reference into this application. The accompanying sequence listing text file, named USC1410-2_ST25.txt, was created on Feb. 24, 2020 and is 4 kB in size. The file can be accessed using Microsoft Word on a computer that uses Windows OS.

FIELD OF THE INVENTION

The invention pertains to the field of non-invasive screening and diagnostics of bladder cancer, including bladder cancer recurrence.

BACKGROUND OF THE INVENTION

In 2011, bladder cancer was one of the ten most prevalent malignancies in males ranking number fourth and number eighth in terms of deaths and new cases, respectively (Siegel, Ward et al. 2011). The most common symptom of bladder cancer is hematuria, and general risk factors for the disease include smoking and carcinogen exposure (Morgan and Clark 2010). Non-muscle invasive bladder cancer (NMIBC) accounts for 80% of all the cases, and can be further classified into papillary (Ta), flat and carcinoma in situ (Tis) and subepithelial connective tissue invaded (T1) lesions. The rest of the cases present as muscle invasive bladder cancer (MIBC) (Sobin, Gospodarowicz et al. 2009, Babjuk, Oosterlinck et al. 2011). The current first line of treatment for NMIBC is transurethral resection of bladder tumor (TURBT); however, 50% of patients will recur after the TURBT procedure, with the highest rate of recurrence occurring in patients with high risk disease (Millán-Rodríguez, Chéchile-Toniolo et al. 2000, Shelley, Mason et al. 2010). As a result, TURBT patients require frequent monitoring and lifelong maintenance treatment, which makes bladder cancer one of the most costly types of cancer in terms of patient management.

The current gold standard for monitoring and treatment of bladder cancer recurrence involves the use of cystoscopy and cytology in combination with intravesical Bacile Calmette-Guerin (BCG) immunotherapy or chemotherapy (Morgan and Clark 2010, Babjuk, Oosterlinck et al. 2011). Disease surveillance is challenging because of the invasive nature of cystoscopic examination, which carries some degree of morbidity, and because of the low sensitivity displayed by urinary cytology in the detection of low-grade tumors (Lintula and Hotakainen 2010). In recent years, efforts have been devoted to find better markers of disease diagnosis and prognosis in samples collected by non-invasive methods, such as urine sediments (Sturgeon, Duffy et al. 2010). Bladder tumor cells have weaker cellular attachment than normal or benign bladder urothelium and therefore they shed more and can be collected in urine (urine sediments). However, due to their poor specificity, the markers proposed to date have not been adopted in routine clinical practice (Parker and Spiess 2011). Therefore, there is an urgent need to find reliable markers to monitor recurrence in TURBT patients, which in turn, may help facilitate and improve disease management.

More recently, it has been proposed that longitudinal collection and testing of urine sediments may help assess the prognostic, monitoring, and recurrence predictive value of markers (Hogue, Begum et al. 2006). Several studies undertook this approach by using DNA methylation analysis, microsatellite markers and a fibroblast growth factor receptor 3 (FGFR3) mutation assay (Roupret, Hupertan et al. 2008, Zuiverloon, van der Aa et al. 2010). Although these markers were highly sensitive, they displayed low specificity, in some cases comparable to that of cytology (Brems-Eskildsen, Zieger et al. 2010). A four DNA methylation marker panel provided better specificity; however, it also displayed a high rate of false-positive results (33%) (Zuiverloon, Beukers et al. 2012). As such, there is continued need for better, more specific and accurate testing methods for bladder cancer and bladder cancer recurrence.

SUMMARY OF THE INVENTION

One object of the present invention is to provide methods, systems and kits useful in the identifying patients in whom bladder cancer has recurred.

Another object of the present invention is to provide methods, systems and kits useful in identifying patents at high risk for the recurrence of bladder cancer.

Another object of the present invention is to provide methods, systems and kits useful in diagnosing bladder cancer.

Another object of the present invention is to offer methods, systems and kits useful in minimizing the frequency of invasive and expensive procedures commonly used in the management of bladder cancer occurrence.

Another object of the present invention is providing a tool that may be useful for deciding to closely monitor or provide individualized treatment for patients with no clinical evidence of bladder cancer but who still maintain aberrant DNA methylation, since they could carry a high risk of recurrence.

One aspect the present invention is a highly accurate and specific multi-DNA Methylation biomarker method for the prognosis, prognosis and diagnosis of bladder cancer and bladder cancer recurrence. For instance, one finding of the present invention is that DNA methylation status of HOXA9, SOX1, NPY, IRAK3, ZO2, and L1-MET was significantly associated with recurrence with high sensitivity and specificity (all p<0·0001), a three-marker signature that included SOX1, IRAK3, and L1-MET had a recurrence predictive power far superior to that of cytology (90% vs. 7% accuracy)

Another aspect of the present invention is a combination of hypermethylated DNA Methylation biomarkers and hypomethylated DNA Methylation biomarker to screen patient test sample.

Another aspect of the present invention is the finding that DNA methylation changes in urine sediments from TURBT patients can be used to detect early bladder cancer recurrence. Specifically, methylation of HOXA9, SOX1, NPY, IRAK3, ZO2 (hypermethylated markers), and demethylation of L1-MET (hypomethylated marker) display a positive correlation with tumor recurrence with high sensitivity and specificity (p<0·0001). The combination of SOX1, IRAK3 and L1-MET markers provides better resolution than cytology and cystoscopy in the detection of early recurrence changes. The methods, kits and systems of the present invention provide a non-invasive and cost-effective way to assess TURBT patients, which if applied to the clinical setting, may help delay or reduce the risk of tumor recurrence and limit the use of invasive procedures such as cystoscopies.

One embodiment of the present invention is a method for the prediction, prognosis and/or diagnosis of bladder cancer or bladder cancer recurrence in a subject, the method comprising:
  providing a test sample from the subject;
  measuring a DNA methylation level of at least a portion of one or more polynucleotides selected from the group consisting of HOXA9, SOX1, NPY, IRAK3, L1-MET, and ZO2 in the test sample;
  comparing the DNA methylation level of the one or more polynucleotides in the test sample to a reference DNA methylation profile based on the DNA methylation levels of the one or more polynucleotides in a control group, members of which had bladder cancer; and
  based on the comparison, determining at least one of: (1) whether bladder cancer has recurred; (2) whether there is likelihood that the bladder cancer will recur; and (3) whether the patient has bladder cancer.

Another embodiment of the present invention is a method for the prediction, prognosis and/or diagnosis of bladder cancer or bladder cancer recurrence in a subject, the method comprising:
  providing a test sample from the subject;
  measuring DNA methylation levels of at least a portion of two or more polynucleotides selected from the group consisting of HOXA9, SOX1, NPY, IRAK3, L1-MET, and ZO2 in the test sample;
  calculating a risk score based on the measured DNA methylation levels,
  comparing the calculated risk score to a cut-off value derived from a reference DNA methylation profile based on DNA methylation levels of the one or more biomarkers derived from a control group, members of which had bladder cancer; and
  based on the comparison calculated risk score to the cut-off value, determining at least one of: (1) whether bladder cancer has recurred; (2) whether there is likelihood that the bladder cancer will recur; and (3) whether the patient has bladder cancer.

Another embodiment of the present invention is a system comprising: a non-transitory computer readable medium comprising a computer readable program code stored thereon for causing a processor to obtain the measured DNA methylation levels of one or more of HOXA9, SOX1, NPY, IRAK3, L1-Met, and ZO2 in the test sample; compare the DNA methylation levels of the one or more biomarkers in the test sample to a reference DNA methylation profile of the one or more biomarkers derived from a control group, members of which had bladder cancer. Preferably, the system includes a report that is generated based on the comparison providing guidance as to one of: (1) whether bladder cancer has recurred; (2) whether there is risk that the bladder cancer will recur; and (3) whether the patient has bladder cancer.

Another embodiment of the present invention is a system comprising a non-transitory computer readable medium comprising computer readable program code stored thereon for causing a processor to obtain the measured DNA methylation levels of two or more of HOXA9, SOX1, NPY, IRAK3, L1-Met, and ZO2 in the test sample; calculate a risk score; and compare the risk score to a cut-off value derived from a reference DNA methylation profile based on DNA methylation levels of the one or more biomarkers derived from a control group, members of which had bladder cancer.

In another aspect, the present invention is directed to a diagnostic test for assessing the likelihood of bladder cancer recurrence. Diagnostic test in accordance with this aspect of the invention will generally comprise an urine processing kit for extracting DNA from urine, and a DNA detection unit specific for detecting a panel of three biomarkers comprising essentially of SOX1, IRAK3, and L1-MET. As demonstrated in the illustrative examples below, DNA may be extracted from urine using any methods, devices, or commercially available kits known in the art. Detection of the three biomarkers can be done by any DNA methylation detection assays, kits, devices known in the art such as PCR, pyrosequencing, but not limited thereto.

In another aspect, the present invention is directed to a method of monitoring recurrence of bladder cancer. Methods in accordance with this aspect of the invention will generally include the steps of obtaining a urine sample from a subject; isolating DNA from said urine sample; and analyzing said DNA for the presence of methylated biomarkers comprising essentially of SOX2, IRAK3, and L1-MET.

Other aspects and advantages of the invention will be apparent from the following description and the appended claims.

BRIEF DESCRIPTION OF THE DRAWINGS

(FIG. 1A) Timeline of longitudinally collected urine sediment samples from bladder cancer patients after tumor resection. Each patient's starting point, denoted by time 0, refers to the first follow-up visit in the study when a urine sample was collected. A follow-up visit marked in red indicates the time of recurrence. (FIG. 1B) Receiver operating characteristic (ROC) curves of HOXA9, SOX1, NPY, IRAK3, ZO2 and L1-MET were created using 31 urine sediments of TURBT patients at first recurrence and 56 urine sediments from the last follow-up of recurrence-free patients. AUC: area under the curve. (FIGS. 1C-1D) Long-term DNA methylation analysis in TURBT patients and its relationship with clinical status in patients who had no recurrence (FIG. 1C) and patients who had recurrence (FIG. 1D). (−): negative; (*): suspicious; (+): positive (biopsy or histologically proven bladder tumor, severe atypia or papillary lesions in cytology or cystoscopy); R: recurrence; BCG: Bacille Calmette Guerin.

FIGS. 2A-2C show that a three-marker signature has high sensitivity and specificity in detecting tumor recurrence. (FIG. 2A) The risk score of −0·37608+0·17095×SOX1+ 0·21604×IRAK3−0·09887×L1-MET was calculated in the urine sediments of TURBT patients with no recurrence at the last follow-up and with recurrence. (FIG. 2B) Five-fold cross-validation showed a sensitivity of 86% and specificity of 89%. (FIG. 2C) This three-marker model was validated in a separate urine sediment samples that included urine sediments from recurrence-free patients before the last follow-up visit (CU) and urine sediments of patients carrying tumors (TU), and the sensitivity and specificity were determined. Risk scores above the cut-off value (dashed line) denote positive scores, while those below signify negative scores.

DETAILED DESCRIPTION OF THE INVENTION

Figure 1A:
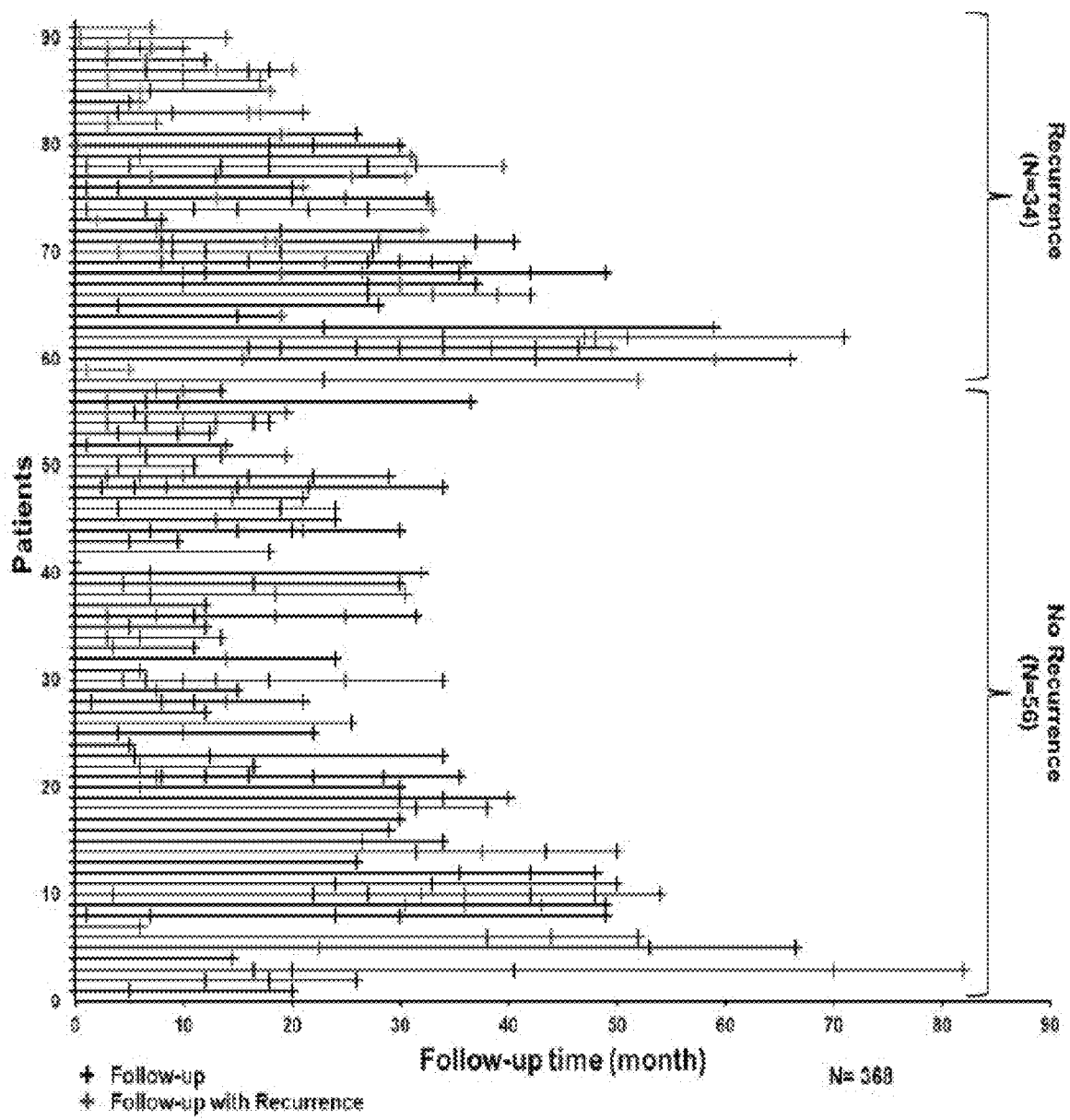
FIGS. 1A-1D show that a panel of six DNA methylation markers tested in urine sediments from TURBT patients was positively correlated with bladder tumor recurrence and has high sensitivity and specificity.

One embodiment of the present invention is directed to a method for the prediction, prognosis and/or diagnosis of bladder cancer in a subject, the method comprising:
  providing a test sample from the subject;
  measuring the DNA methylation levels of one or more of HOXA9, SOX1, NPY, IRAK3, L1-MET, and ZO2 in the test sample;
  comparing the DNA methylation levels of the one or more biomarkers in the test sample to a reference DNA methylation profile of the one or more biomarkers derived from a control group, members of which had bladder cancer; and
  based on the comparison, determining at least one of: (1) whether bladder cancer has recurred; (2) whether there is likelihood that the bladder cancer will recur; and (3) whether the patient has bladder cancer.

As used herein, bladder cancer recurrence refers to biopsy-proven bladder cancer occurring subsequent to resection of a visible primary tumor. Bladder cancer recurrence may also include severe atypia concomitant with papillary lesions detected by cytology and cystoscopy when biopsy results are not available. Where appropriate in connection with either a test subject or a control group, tumors may be characterized according to the criteria of the American Joint Committee on Cancer (World Health Organization/International Society of Urological Pathology (ISUP); ref 26) and staging was based on the tumor—node—metastasis classification (International Union Against Cancer).

The subjects who may benefit from the methods, kits and systems of the present invention include those who have or are at risk for developing bladder cancer or bladder cancer recurrence. In general, bladder cancer, including either NMIBC or MIBC, will be diagnosed by a physician based on standard clinical practice and testing. The subject who may benefit from the methods, kits and systems of the present invention are generally mammals. In a preferred embodiment, the subject is a human patient who has been diagnosed with non-muscle invasive bladder cancer (NMIBC), and more preferably, is a patient who has already undergone at least one bladder cancer treatment procedure prior to collection of a test sample. In a particularly preferred embodiment, the patient has been previously undergone TURBT and is under surveillance for tumor recurrence after the TURBT procedure. Alternatively, the patient may have muscle invasive bladder cancer (MIBC).

The methods of the present invention generally include providing a test sample from a subject. The biological source of a test sample obtained from the subject that is to be used in connection with the present invention is not particularly limited, so long as the DNA methylation status (or levels) of the polynucleotides of interest (i.e., selected from HOXA9, SOX1, NPY, IRAK3, L1-MET, and ZO2) in the test sample minors that of a bladder cancer tumor. This may be verified in accordance with the methods and procedures discussed in the Examples set forth herein. Preferably, The test samples obtained from the subject obtained using a non-invasive or minimally invasive procedures.

In a preferred embodiment, the test sample is a urine sample. Urine specimens may include samples from both "urine" and "bladder wash." If bladder wash is selected, the bladder wash may be collected at the time of cystoscopy by a nurse or a urologist. Typical volumes of urine sample may be around 50 ml. In another embodiment, the test sample is a blood sample containing bladder cancer CTCs (circulating tumor cells). Urine or blood samples may be subjected to a number of procedures to place the sample in a form suitable for DNA extraction and DNA methylation analysis. For example, urine samples may be centrifuged for, by example 10 min at 1500 g, for subsequent DNA extraction from urine sediments. (See Friedrich, Weisenberger et al. 2004).

The methods of the present invention generally include measuring the DNA methylation levels of one or more of HOXA9, SOX1, NPY, IRAK3, L1-MET, and ZO2 in the test sample. As used herein, DNA methylation refers to the introduction of a methyl group in the 5-position of the cytosine residue of CpG dinucleotides. In normal cells, CpG-rich regions or CpG islands located at specific promoter regions are usually unmethylated thereby allowing transcriptional activity, whereas methylation occurs in some repetitive elements resulting in their silencing (Jones 1999, Jones 2002, De Carvalho, Sharma et al. 2012). Aberrant DNA methylation is both one of the earliest and the most common epigenetic change that occurs during tumorigenesis and it can be detected in premalignant lesions (Wolff, Byun et al. 2010, Wolff, Chihara et al. 2010, Jones 2012). Inactivation of tumor suppressor genes by gain of DNA methylation (hypermethylation) or global loss of DNA methylation (hypomethylation), which activates genes that are normally not expressed have been both observed in bladder tumors (Jurgens, Schmitz-Drager et al. 1996, Kim and Kim 2009). Changes in DNA methylation can also be stable and be quantified (Laird 2003, Wolff, Liang et al. 2005).

The biomarkers useable in connection with the present invention are the DNA methylation levels of at least a portion of one or more of the following polynucleotide: HOXA9, SOX1, NPY, IRAK3, L1-MET, and ZO2. Here, "IRAK3" refers to the IRAK3 gene, i.e., the interleukin-1 receptor-associated kinase 3 protein-coding gene. "HOXA9" refers to the HOXA9 gene, the homeobox A9 protein-coding gene. "NPY" refers to the NPY gene, the neuropeptide Y protein-coding gene. "SOX1" refers to the SOX1 gene, the SRY (sex determining region Y)-box 1 protein-coding gene. "L1-Met" refers to the Line 1 promoter located within the MET oncogene. "ZO2" is also known as "TJP2" refers to the TJP2 gene, the tight junction protein 2 is a protein-coding gene. The region of interest for DNA Methylation measurement, analysis and characterization in the selected polynucleotides preferably includes at least CpG-rich region or CpG island, more preferably located at one or more specific promoter regions of the selected genes. The LINE1 element, which is located within the MET oncogene (L1-MET) activates an alternate transcript of MET and is hypomethylated. The promoter of ZO2 is hypermethylated in bladder tumors as well as in adjacent histologically normal urothelium, suggesting that epigenetic changes precede morphological changes, a phenomenon termed epigenetic field defect. HOXA9, SOX1, NPY, IRAK3 are also hypermethylated in bladder tumor cancer cells relative to on-tumor bladder cells.

DNA Methylation levels may generally be expressed as the percentage of methylated cytosines, which is the number of methylated cytosines divided by the sum of the number of methylated cytosines plus the number of unmethylated cytosines. DNA methylation Levels may be obtained from the test sample using methods generally known and available to those ordinarily skilled. These methods may generally include steps of DNA extraction from the test sample, bisulfite conversion and PCR amplification of the regions of interest. By way of example, DNA in the test sample may be bisulfite converted using, for instance, an EZ DNA Methylation Kit (Zymo Research) according to the manufacturer's instructions. The regions of interest of the selected genes may be PCR amplified using the biotin-labeled primers of Table 4 and analyzed by pyrosequencing, a high-throughput and quantitative tool for DNA sequence detection. In a preferred embodiment, DNA Methylation Levels, which may be defined as the percentage of methylated cytosines, which is the number of methylated cytosines divided by the sum of methylated and unmethylated cytosines, may be measured using PSQ HS96 (Qiagen). Those of ordinary skill in the art will recognize these. Those of ordinary skill in the art will recognize that the methods of alternative methods of sequencing and DNA methylation may equally be suitable.

When one and only one biomarker is selected from HOXA9, SOX1, NPY, IRAK3, L1-MET, and ZO2, the step of comparing the DNA methylation levels of the selected biomarker to the reference DNA methylation profile, generally comprises comparing the DNA Methylation level of the selected biomarker to a cut-off level generated from the DNA Methylation Profile of a control group who had bladder cancer, and based on the comparison of the DNA Methylation Level of the test sample to the cut-off value, a determination is made of at least one of: (1) whether bladder cancer has recurred; (2) whether there is likelihood that the bladder cancer will recur; and (3) whether the patient has bladder cancer.

Although DNA methylation levels of individual polynucleotides selected from the group consisting of HOXA9, SOX1, NPY, IRAK3, L1-Met, and ZO2 may be used to practice the invention, it is preferable that the DNA methylation levels of at least two or more of HOXA9, SOX1, NPY, IRAK3, L1-Met, and ZO2 are used to generate a "DNA methylation profile." When two or more are used, this may be referred to a "panel" of biomarkers. Further, a "profile" generally includes any set of data that represents the distinctive features or characteristics associated with bladder cancer. The "DNA methylation profile" comprises a set of methylation data that represents the DNA methylation levels (e.g., methylation status) of two or more polynucleotides selected from the group consisting of HOXA9, SOX1, NPY, IRAK3, L1-Met, and ZO2. Preferably, the DNA Methylation profile includes at least DNA Methylation data regarding at least one hypomethylated polynucleotide (i.e., L1-Met) and at least one hypermethylated polynucleotide (i.e., HOXA9, SOX1, NPY, IRAK3, L1-Met, and ZO2). In an especially preferred embodiment the DNA methylation profile comprises DNA methylation data for at least SOX1, IRAK3, and L1-MET. The number and identity of the selected panel of biomarkers is not particularly limited so long as there is sufficient accuracy and specificity as set forth herein. Preferably, the selected panel of data is at least as accurate and specific as the panel of SOX1, IRAK and L1-MET as set forth herein.

When a panel of two or more biomarkers is selected, the step of comparing the DNA methylation levels of the selected panel of markers to the reference DNA methylation profile, generally comprises the calculation of a risk score, wherein, based on the risk score, patient is classified as having recurrent bladder cancer or a likelihood of developing recurrent bladder cancer. The risk score may be obtained using a logistic regression analysis as disclosed herein. In one embodiment, the risk score represents the probability of a positive result (recurrence) on the log-odds scale. The risk score may be compared to cut-off value generated from the DNA Methylation Profile of a control group who had bladder cancer, and based on the comparison of the risk score to the cut-off value, a determination is made of at least one of: (1) whether bladder cancer has recurred; (2) whether there is likelihood that the bladder cancer will recur; and (3) whether the patient has bladder cancer. In one embodiment, the cut off value is 0. On this scale, a score of 0 represents a probability of 0.5 (50% chance) for a patient having recurrence. Preferably, on this scale, the cutoff of the risk score to predict recurrence is 0, with scores >0 having a more than 50% chance of being from a recurrent patient, and scores <0 having a less than 50% chance of being from a recurrence patient. In a preferred embodiment, the risk score is multi-variate equation based on the DNA Methylation levels of each of the selected panel members. For example, where the panel is SOX1, IRAK3, and L1-MET, the risk score for the control group of the examples was determined to be:

$$R = -0.37608 + 0.17095 \times M_{SOX1} + 0.21604 \times M_{IRAK3} - 0.09887 \times M_{L1\text{-}MET}$$

Wherein R is the risk score, and $M_{SOX1}$, $M_{IRAK3}$, and $M_{L1\text{-}MET}$, are the methylation levels (expressed as the percentage of methylated cytosines) of SOX1, IRAK3 and L1-MET, respectively.

Figures 4A, 4B:
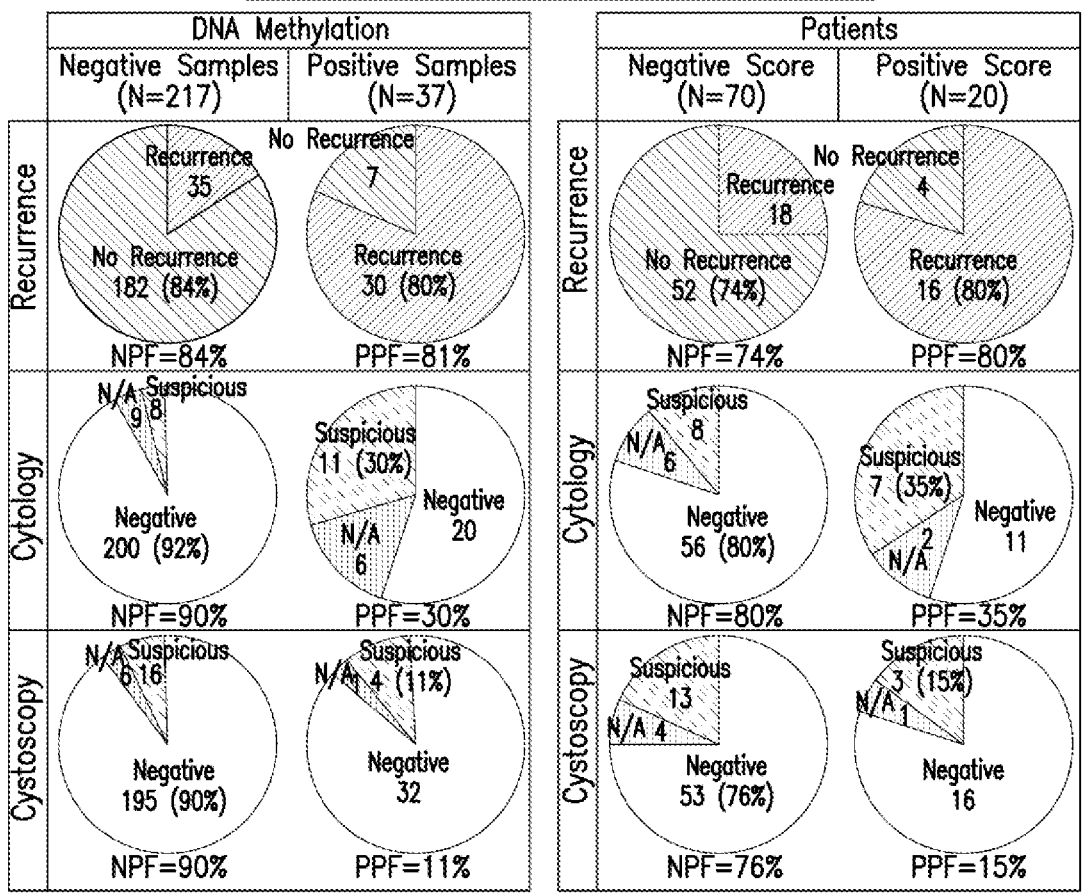
FIGS. 4A-4C show that three DNA methylation markers help predict the risk of recurrence of bladder tumors in urine sediments. Percentage of urine sediments that had positive scores (DNA methylation score calculated to be higher than cut-off values) at the time of recurrence (N=38) (FIG. 4A), in the period before recurrence for recurrence-free patients (N=189) and for patients who ultimately had recurrence (N=65) (FIG. 4B), and at any time for recurrence-free patients (N=189) and for recurrence patient (N=103) (FIG. 4C), and the comparison with cytology and cystoscopy reports at the same visits to the clinic. Pie charts summarize all sample (left) or patients (right) in the period before recurrence (FIG. 4B), or at any time (FIG. 4C). A patient-level positive score represents a history of positive DNA methylation scores at any eligible visits. Sample-level charts report the percentage of samples from recurrence-free patients in DNA methylation negative samples (Negative Predictive Fraction, NPF) and the percentage of samples from patients with recurrence in DNA methylation positive samples (Positive Predictive Fraction, PPF); patient-level charts report the percentage of recurrence-free patients in those without a history of positive samples (Negative predictive value, NPV) and percentage of patients with recurrence in those with a history of DNA methylation positive samples (positive predictive value, PPV). Also reported are the cytological and cystoscopic performance in these same groups of samples/patients.

Positive risk scores may be used to determine bladder cancer recurrence, For instance, as described herein, in one example, positive risk scores were found in 90% of the samples (34/38) at the time of recurrence diagnosis, exceeding the sensitivity of both cytology (16%) and cystoscopy (8%). Further, Eighty percent of patients (16/20) whose urine samples showed a history of positive risk scores developed recurrence later (95% CI, 62%-98%). Out of the 70 patients who did not have a history of positive DNA methylation scores, 52 (74%) did not recur (95% CI, 64%-85%; FIG. 4B). Further, the risk score can also help guide treatment decisions in connection with a treating physician, such as minimizing the frequency of cystoscopy for patients with a negative risk score. Patients with a positive risk score but no clinical evidence of bladder cancer disease should still be closely monitored because they carry a high risk of recurrence.

On aspect of the present invention is a method for developing an appropriate combination of markers capable of detecting tumor recurrence or the likelihood of recurrence in test samples that is characterized by high sensitivity and specificity, wherein the biomarkers are selected from the DNA Methylation levels of one or more of HOXA9, SOX1, NPY, IRAK3, L1-MET, and ZO2. Receiver operating characteristic (ROC) curves are generated that summarize the accuracy of DNA markers in test samples from control subjects who have previously been diagnosed with bladder cancer. The test sample are preferably selected at least one of: (1) the time of diagnosis; (2) the time of the last follow-up visit after TURBT (non-recurrent patients), or at the time of first recurrence (patients with recurrence after TURBT). Preferably, only the subset of patients with complete data on all markers is used to generate the risk score as a multivariable predictor model.

A stepwise logistic regression analysis of the data should be used, selecting variables to add or subtract based on the Akaike Information Criterion (AIC). The AIC is the optimality criterion used for model selection. When comparing two models, the model with the lowest AIC is preferred. We compare the AIC of the model with no variables to the AIC of all 1-variable models, and add the variable reducing the AIC the most. This is repeated, by adding the next variable that further reduces the AIC. This forward step is repeated once more, with the addition of a backward step that evaluates the possibility of removing one of the variables already in the model. For each new step, the addition/removal of a variable is considered, providing a means of "stepping" through models with different combination of variables, to search for the best predictive model. The procedure ends when the model with the lowest AIC is found.

The risk score obtained using logistic regression represents the probability of a positive result (recurrence) on the log-odds scale. On the preferred scale, a score of 0 represents a probability of 0.5 (50% chance) for a patient having recurrence. This suggests that the best cutoff of the risk score to predict recurrence is 0, with scores >0 having a more than 50% chance of being from a recurrent patient, and scores <0 having a less than 50% chance of being from a recurrence patient.

Sensitivity and specificity may be estimated using 5-fold cross-validation, repeating the model selection for each subdivision of the data. Five-fold cross-validation was used to obtain the reported (less biased) estimates of sensitivity and specificity. Model selection was performed using forward and backward stepwise selection on four fifths of the dataset, and the predictive ability assessed on the fifth that was not used for variable selection, an independent data subset. Preferably, this is repeated five times, each time holding a separate fifth of the dataset out for validation, and performing a new model selection on the remaining four fifths.

One or more embodiments of the invention may be implemented on a computer. For instance, any of the DNA Methylation levels, statistical analysis, comparisons and risk scores may derived, implemented, stored or processed by a computer. Further, any determination or evaluation may likewise be derived, analyzed or reported by a computer. The type computer is not particularly limited regardless of the platform being used. For example, a computer system generally includes one or more processor(s), associated memory (e.g., random access memory (RAM), cache memory, flash memory, etc.), a storage device (e.g., a hard disk, an optical drive such as a compact disk drive or digital video disk (DVD) drive, a flash memory stick, magneto optical discs, solid state drives, etc.), and numerous other elements and functionalities typical of today's computers or any future computer (not shown). Each processor may be a central processing unit and may or may not be a multi-core processor. The computer may also include input means, such as a keyboard, a mouse, a tablet, touch screen, a microphone, a digital camera, a microscope, etc. Further, the computer may include output means, such as a monitor (e.g., a liquid crystal display (LCD), a plasma display, or cathode ray tube (CRT) monitor). The computer system may be connected to a network (e.g., a local area network (LAN), a wide area network (WAN) such as the Internet, or any other type of network) via a network interface connection, wired or wireless (not shown). Those skilled in the art will appreciate that many different types of computer systems exist, and the aforementioned input and output means may take other forms including handheld devices such as tablets, smartphone, slates, pads, PDAs, and others. Generally speaking, the computer system includes at least the minimal processing, input, and/or output means necessary to practice embodiments of the invention.

Further, those skilled in the art will appreciate that one or more elements of the aforementioned computer system may be located at a remote location and connected to the other elements over a network. Further, embodiments of the invention may be implemented on a distributed system having a plurality of nodes, where each portion of the invention may be located on a different node within the distributed system. In one embodiment of the invention, the node corresponds to a computer system. Alternatively, the node may correspond to a processor with associated physical memory. The node may alternatively correspond to a processor or micro-core of a processor with shared memory and/or resources. Further, computer readable program code (e.g., software instructions) to perform embodiments of the invention may be stored on a computer readable medium. The computer readable medium may be a tangible computer readable medium, such as a compact disc (CD), a diskette, a tape, a flash memory device, random access memory (RAM), read only memory (ROM), or any other tangible medium.

Thus, one embodiment of the present invention is directed to system comprising: a non-transitory computer readable medium comprising computer readable program code stored thereon for causing a processor to obtain the measured DNA methylation levels of one or more of HOXA9, SOX1, NPY, IRAK3, L1-Met, and ZO2 in the test sample; and compare the DNA methylation levels of the one or more biomarkers in the test sample to a reference DNA methylation profile of the one or more biomarkers derived from a control group, members of which had bladder cancer. In a preferred embodiment, a report is generated based on the comparison providing guidance as to one of: (1) whether bladder cancer has recurred; (2) whether there is risk that the bladder cancer will recur; and (3) whether the patient has bladder cancer.

Thus, another embodiment of the present invention is directed to a system comprising: a non-transitory computer readable medium comprising computer readable program code stored thereon for causing a processor to obtain the measured DNA methylation levels of two or more of HOXA9, SOX1, NPY, IRAK3, L1-Met, and ZO2 in the test sample; and calculate a risk score. In a preferred embodiment, a report is generated providing guidance based on the risk score as to one of: (1) whether bladder cancer has recurred; (2) whether there is risk that the bladder cancer will recur; and (3) whether the patient has bladder cancer.

Another embodiment of the present is a test kit, optionally together with written instructions for performing an evaluation of relevant comparison or risk score in order to diagnose or assist in the diagnosis of the recurrence of bladder cancer in a patient or to predict the likelihood of recurrence of bladder cancer in a subject.

The kits in accordance with the present invention generally include one or more of the reagents necessary for (optionally together with appropriate instructions for): DNA extraction from the test sample, bisulfite conversion of the extracted DNA; PCR amplification of the regions of interest, pyrosequencing the amplified regions of interest, and measuring the percentage of methylated cytosines. By way of example, DNA in the test sample may be bisulfite converted using, for instance, an EZ DNA Methylation Kit (Zymo Research) according to the manufacturer's instructions. The regions of interest may be PCR amplified using the biotin-labeled primers of Table 4 and analyzed by pyrosequencing, a high-throughput and quantitative tool for DNA sequence detection. The percentage of methylated cytosines, which is the number of methylated cytosines divided by the sum of methylated and unmethylated cytosine.

The DNA Methylation markers of the present invention may also be used in combination with other known markers capable of predicting progression, thereby increasing their predictive accuracy.

EXEMPLIFICATION

Example 1

DNA Methylation Status of Biomarkers in Urine Sediments Mirror that of Tumor

Figure 5:
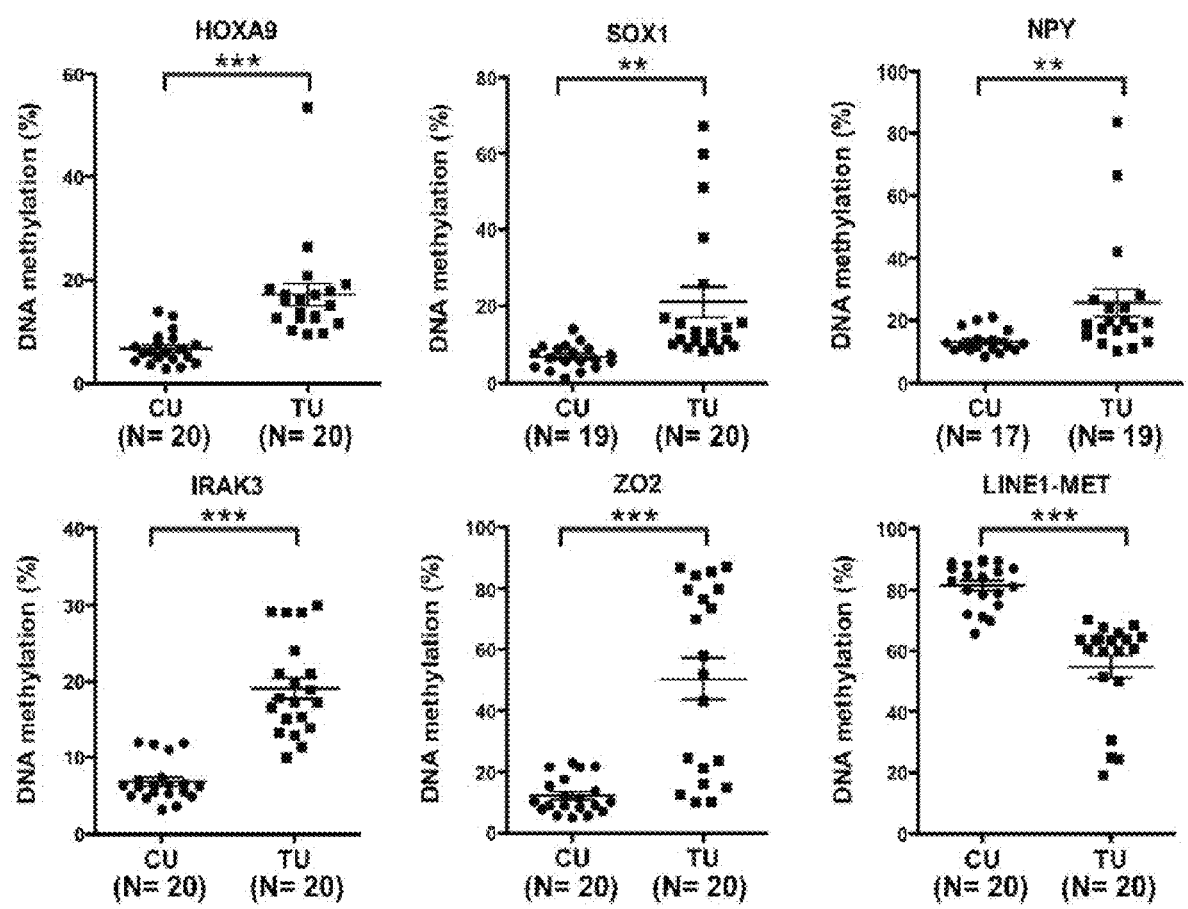
FIG. 5 shows that DNA methylation alterations can be detected in urine sediment samples from patients with bladder cancer. The DNA methylation status of HOXA9, SOX1, NPY, IRAK3, ZO2 and L1-MET was analyzed by pyrosequencing in control urine sediments from cancer-free individuals (CU) and in urine sediments from bladder cancer patients (TU). Paired t-test was performed. : $p<0·01$; *: $p<0·001$.

We previously showed that HOXA9, SOX1, NPY, IRAK3, and ZO2 are hypermethylated in bladder tumor samples (Wolff, Chihara et al. 2010). In addition, we demonstrated that hypermethylation of ZO2 or hypomethylation of L1-MET occurs in tumors as well as in adjacent normal tissues (epigenetic field defect), which may contribute to tumor recurrence (Wolff, Byun et al. 2010, Wolff, Chihara et al. 2010). To evaluate whether hypermethylation of HOXA9, SOX1, NPY, IRAK3 and ZO2, and hypomethylation of L1-MET could also be detected in urine sediments, we analyzed urine samples collected from patients with bladder tumors (n=20) and from age-matched cancer-free controls (n=20) using pyrosequencing. The results show that DNA methylation of HOXA9 ($p<0.0001$), SOX1 ($p=0.0017$), NPY ($p=0.005$), IRAK3 ($p<0.0001$) and ZO2 ($p<0.0001$) was significantly increased, while methylation of L1-MET ($p<0.0001$) was significantly decreased in urine sediments from cancer patients compared to healthy donors, indicating that the methylation status of these DNA methylation and epigenetic field defect markers in urine sediments mirror that of the tumor (FIG. 5).

Example 2

Figure 1B:
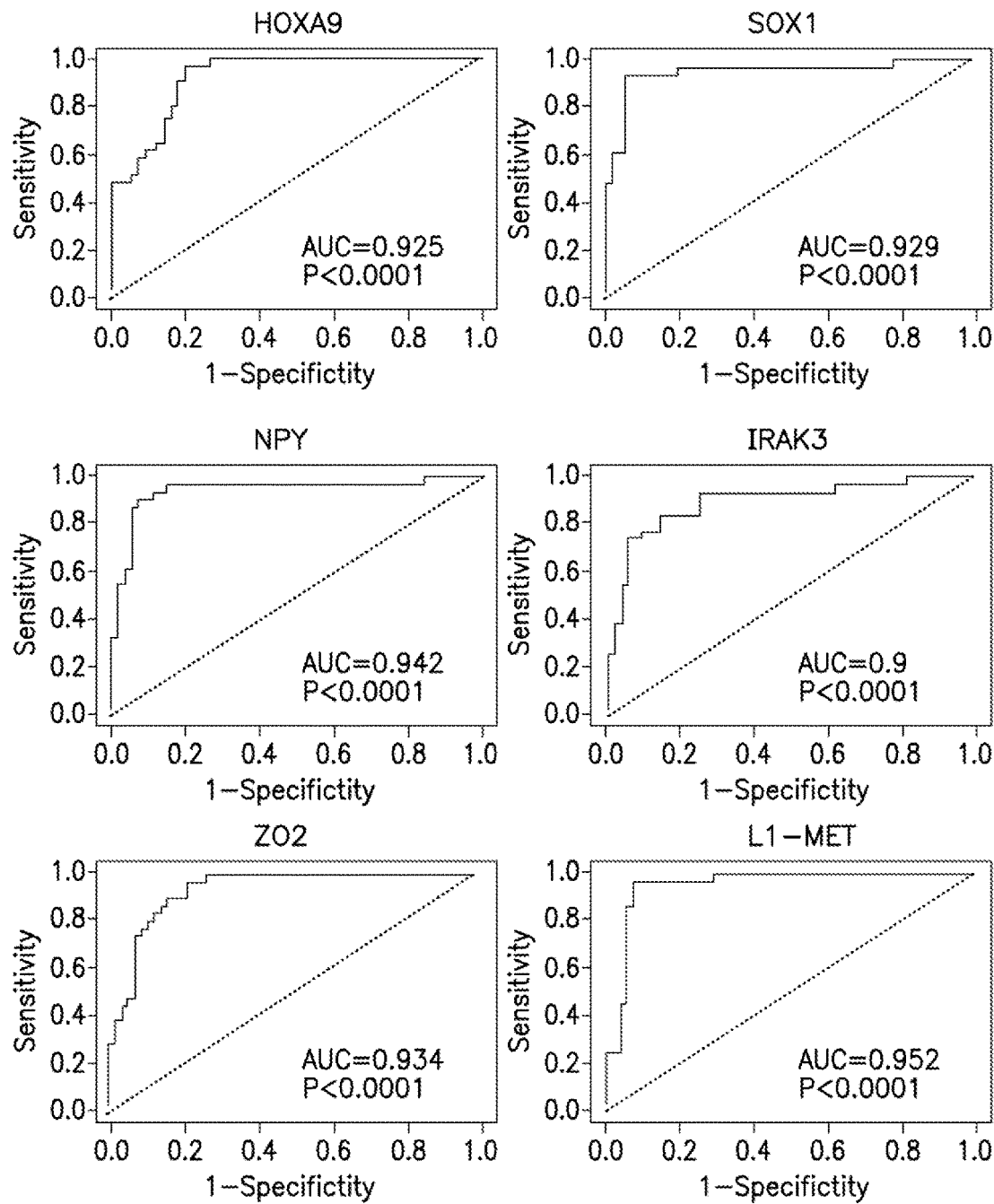
Figure 1C:
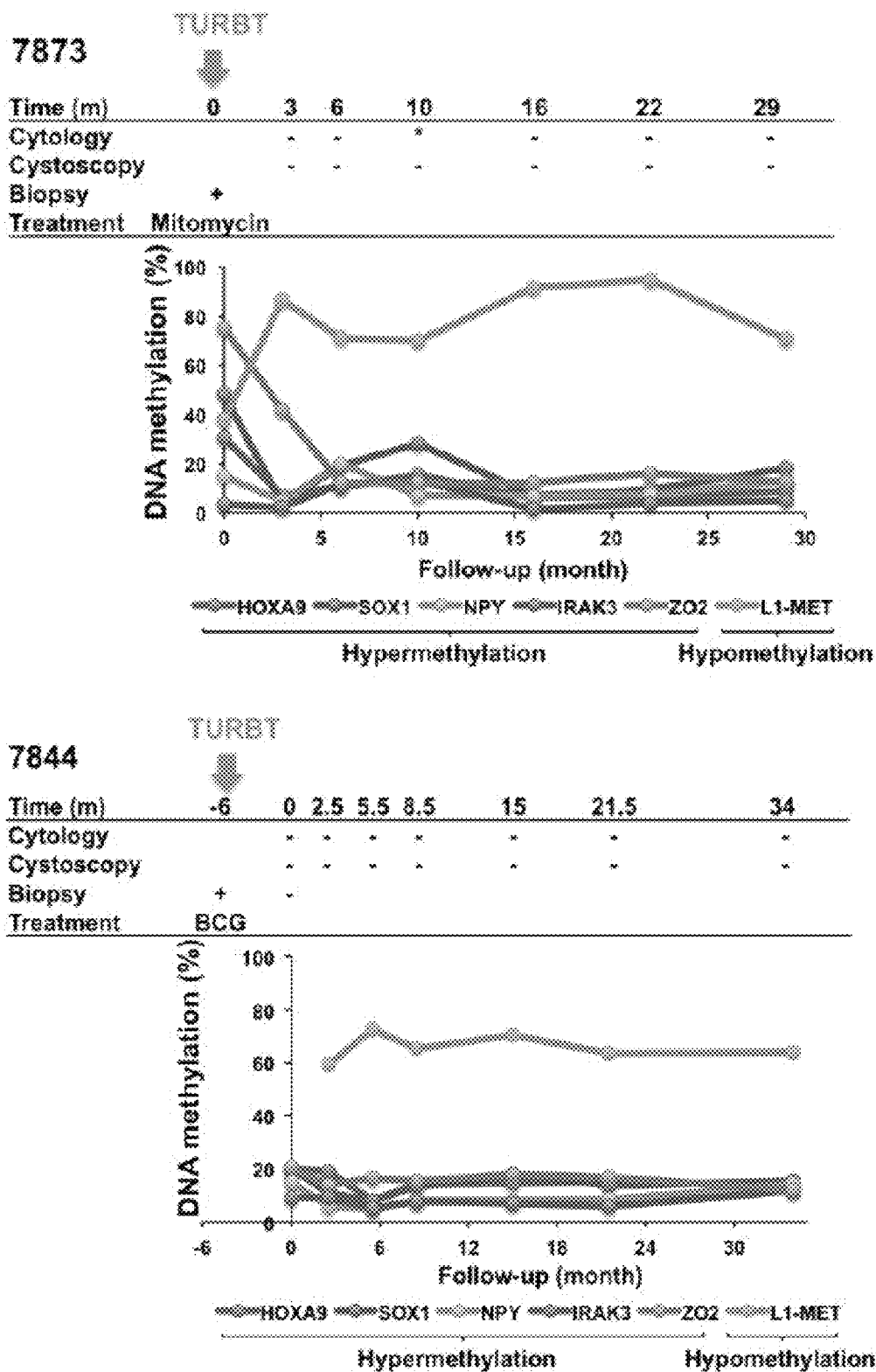
Figure 1D:
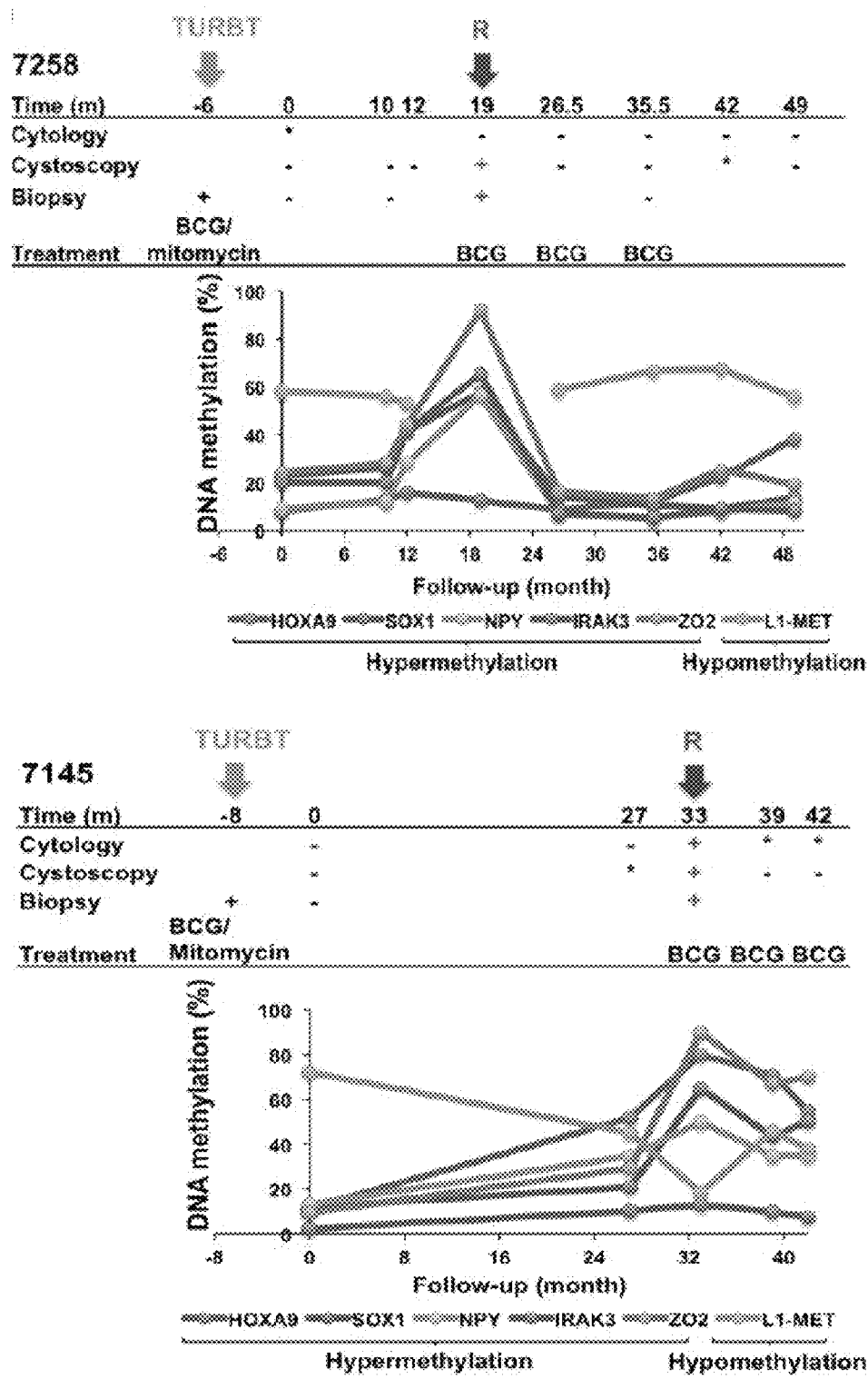
Figure 6:
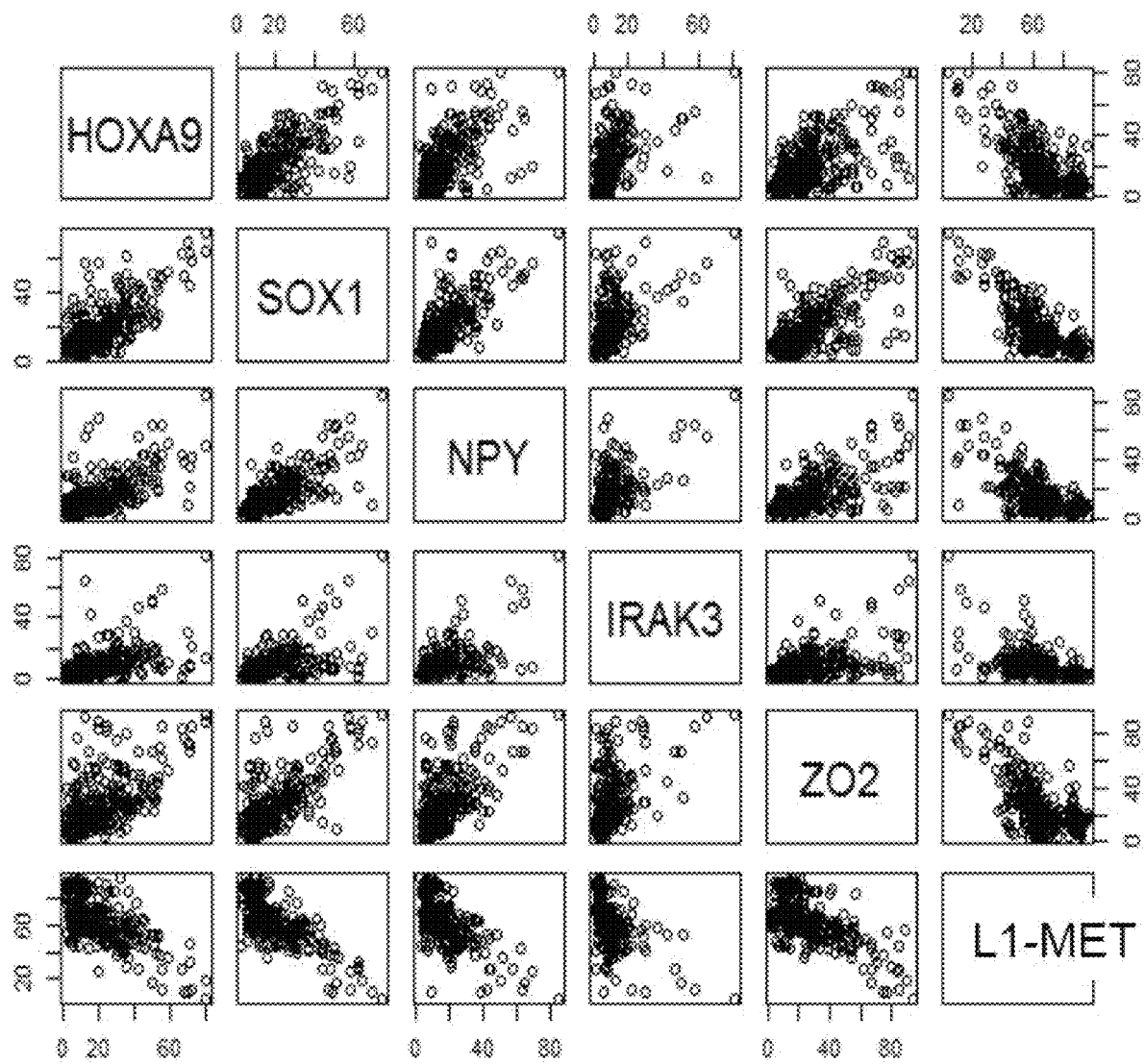
FIG. 6 shows an exemplary Spearman correlation of DNA methylation levels of each marker in urine sediment samples of TURBT patients.

Methylation Status of the Selected Biomarkers Significantly Correlates with Recurrence of Bladder Cancer and have Predictive Value To examine whether aberrant DNA methylation of HOXA9, SOX1, NPY, IRAK3, ZO2 (hypermethylated) and L1-MET (hypomethylated) in urine sediments is associated with tumor recurrence, we first analyzed their DNA methylation status in 368 urine sediments collected in follow-up visits from patients that had undergone tumor resection (FIG. 1A) and calculated the Spearman correlation of DNA methylation level for each marker (FIG. 6). Individual DNA methylation marker success rates averaged 98.9% across all samples (range=94.9-100%). Next, the DNA methylation status of these markers in 31 urine sediments from patients collected at the time of first recurrence was compared to that of 56 samples from the last follow-up visit of patients who did not recur within the study period. Our results show that the six candidate markers individually showed high sensitivity and specificity in recurrence detection as evidenced by the ROC curves and AUC values of 0.93 (HOXA9), 0.95 (SOX1), 0.94 (NPY), 0.9 (IRAK3), 0.93 (ZO2), and 0.95 (L1-MET) ($p<0.0001$; FIG. 1B). Marker methylation analysis is shown in Table 3. In the group of patients without bladder tumor recurrence, urine sediment samples showed consistent DNA methylation levels throughout the duration of surveillance follow-up visits; all the markers methylated in bladder tumors displayed low methylation levels whereas the marker hypomethylated in bladder tumors (L1-MET) maintained high methylation levels after TURBT (FIG. 1C; patients 7873 and 9214). In contrast, the group of patients who had bladder tumor recurrence displayed changes in the DNA methylation status of all six markers at the time of clinically defined recurrence. For example, in patient 7258 DNA methylation levels of hypermethylated markers SOX1, NPY, IRAK3, and ZO2 continued to increase until recurrence was confirmed with a positive cystoscopy and biopsy 19 months after the first urine sample was obtained. Following resection surgery, a decrease in previously elevated methylation levels can be seen (FIG. 1D). A similar pattern was observed in patient 7145; however, the overall methylation levels measured at first recurrence still held at follow-up visits at six and nine months after re-TURBT. This suggests incomplete removal of the recurrent tumor, as suspicious cytology was recorded at these follow-up visits (FIG. 1D). Our results demonstrate that hypermethylation of HOXA9, SOX1, NPY, IRAK3, ZO2 and hypomethylation of L1-MET are consistent with disease recurrence. Furthermore, the methylation levels of these markers displayed a clear trend in the samples obtained at follow-up visits leading to the confirmation of recurrence: hypermethylated markers continued to increase, while those of the hypomethylated markers decreased (FIG. 1D). Taken together, the results demonstrate that the methylation status of these markers in urine sediments not only shows a significant correlation with recurrence ($p<0.0001$), but also has predictive value, as methylation changes could be detected prior to clinical evidence of recurrence.

Example 3

The Selected Biomarkers can Detect Disease Recurrence with High Sensitivity and Specificity To determine the combination of markers capable of detecting tumor recurrence in urine sediments with the highest sensitivity and specificity, we built a model of multiple markers and tested it on 29 samples taken at the time of first recurrence after TURBT, and 54 samples from patients who were recurrence-free at the last time of urine collection. From this model, SOX1, IRAK3, and L1-MET were found to be the best possible marker combination (risk score=$-0.37608+0.17095\times SOX1+0.21604\times IRAK3-0.09887\times L1\text{-MET}$). Scores above zero predict recurrence. Among the 54 samples from patients with no recurrence, we found that 94% of cases showed negative scores (methylation score lower than the cut-off), with three cases displaying positive scores (5.6%). Importantly, among the 29 samples from patients with recurrence, 93% showed positive scores for the presence of recurrence ($p<0.0001$; FIG. 2A). In addition, five-fold cross-validation analysis estimated that these markers can discriminate between recurrent and non-recurrent patients with a sensitivity of 86% and specificity of 89% (FIG. 2B). This three-gene model was then validated using the remaining samples in our cohort: 23 samples taken at a visit where bladder tumors were present (TU, nine recurrences after the first recurrence, and 14 at the time of entry into the study), and 135 samples from patients who had not developed cancer during a given follow-up time (CU). Notably, the three-marker model also showed high sensitivity (83%) and specificity (97%) in the validation sample set: 131 urine sediment samples from patients with no recurrence displayed methylation negative scores whereas 19 urine sediment samples taken from a patient carrying tumors displayed a positive methylation score (FIG. 2C; $p<0.0001$). The DNA methylation status of our three-marker model showed no correlation with any of the primary tumor characteristics, irrespective of tumor recurrence; however, a positive correlation was found between DNA methylation status and tumor grade of the recurrent tumor (table 5). These results demonstrate that the combination of two tumor-specific hypermethylated markers SOX1 and IRAK3, and the field defect hypomethylated marker L1-MET can detect disease recurrence with high sensitivity and specificity. The results also suggest that a balance between hyper- and hypo-DNA methylation is important for bladder carcinogenesis, further establishing the epigenetic field defect as a factor involved in malignant predisposition.

Example 4

The Selected DNA Methylation Markers Reliably Predict Recurrence with a Low False-Positive Prediction Rate (7%)

Figure 3A:
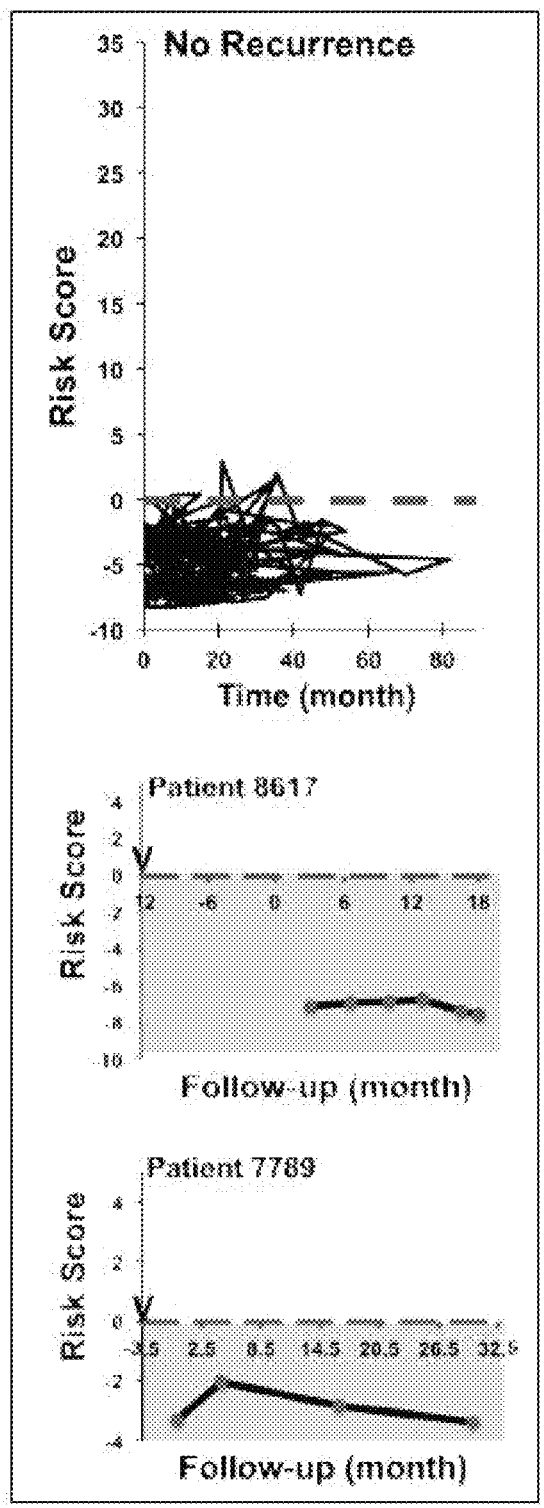
FIGS. 3A-3B show that risk scores given by the combination of three DNA methylation markers help predict the risk of recurrence of bladder tumors in urine. DNA methylation levels of the three-marker combination were used to calculate the risk score for recurrence in the urine sediment samples from TURBT patients who had no recurrence (FIG. 3A) or had recurrence (FIG. 3B) and of two individual patients. V: TURBT operation; R: recurrence; risk score=− 0·37608+0·17095×SOX1+0·21604×IRAK3−0·09887×L1-MET. The dashed line indicates the cut-off value. The orange arrow represents positive scores before recurrence.
Figure 3B:
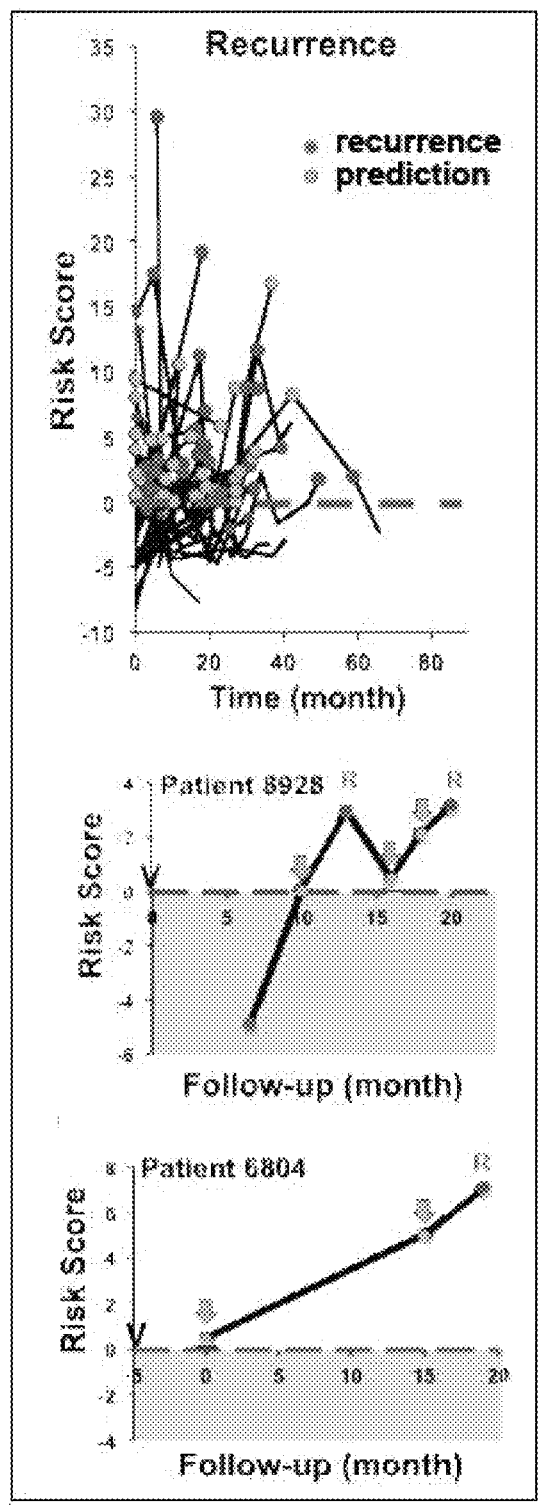
Figure 4C:
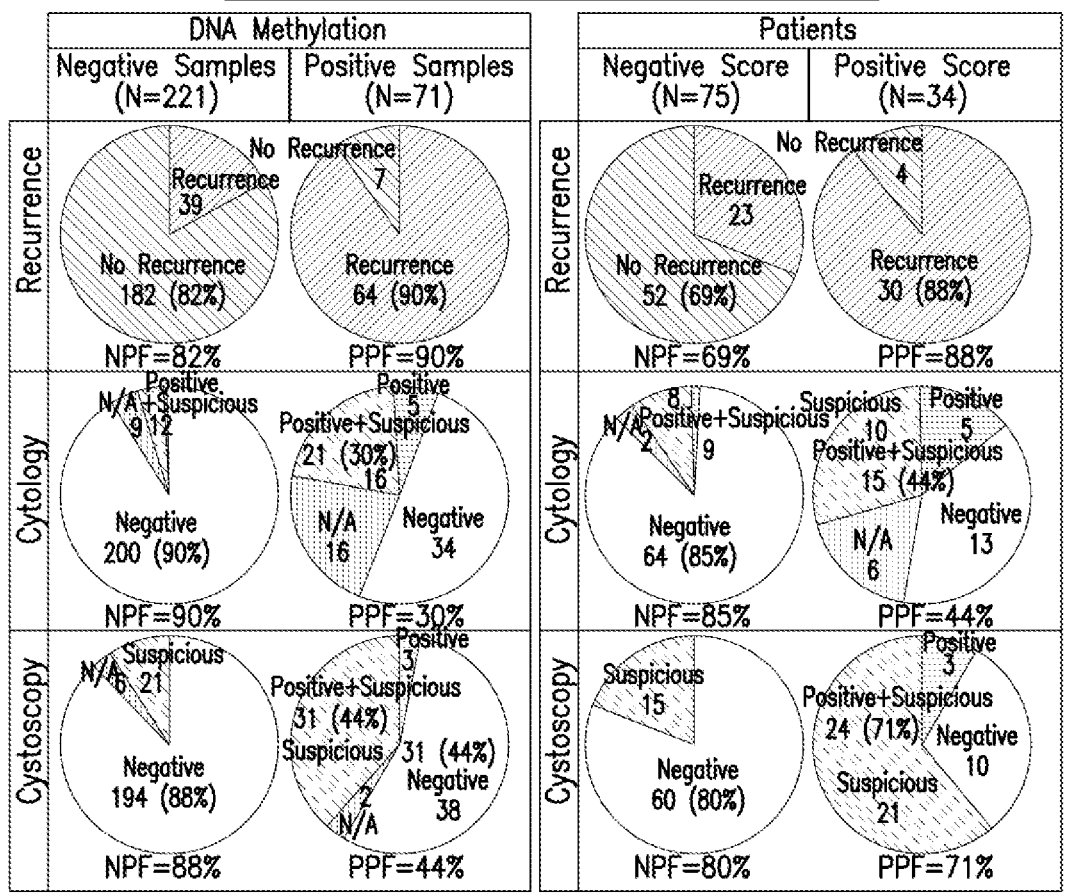

To evaluate whether methylation of the three-marker model predicts recurrence in our longitudinal study samples, we screened DNA methylation and calculated risk scores ($-0.37608+0.17095\times SOX1+0.21604\times IRAK3-0.09887\times L1\text{-MET}$) in every urine sample obtained at follow-up visits from 90 TURBT patients. DNA methylation risk scores given by the combination of SOX1, IRAK3 and L1-MET in the no recurrence group post-TURBT (CU samples reported in FIG. 2C) were lower than the cut-off value throughout months of continuous monitoring (FIG. 3A; patients 8617 and 7789). In contrast, in the group of patients with tumor recurrence, DNA methylation scores changed and showed higher than cut-off values (FIG. 3B). Positive DNA methylation scores were also found in 90% of the samples (34 out of 38) at the time of recurrence diagnosis. The sensitivity of these markers is superior to that of both cytology (16%) and cystoscopy (8%) when considering the same visits to the clinic (FIG. 4A). Furthermore, DNA methylation scores were higher than the cut-off value in urine sediments collected before recurrence, in some cases at least five months prior to the clinical diagnosis of recurrence (FIG. 3B; patients 8928 and 6804). To quantify the prediction value of the three markers, we analyzed risk scores in the period before recurrence in 189 samples from recurrence-free patients and 65 samples from patients who ultimately had recurrence. By analyzing all samples (anytime visits), we found 62% (64 out of 103 urine samples) positive DNA methylation scores in the recurrence group and only 4% (7 out of 189 urine samples) positive scores in the no recurrence group (FIG. 2A, FIG. 2C, FIG. 4C). This represents a 10- and 20-fold increase in the number of samples detected months or years before recurrence compared to urine cytology (6%) or cystoscopy (3%), respectively (FIG. 4C). Furthermore, our results show that out of 71 samples with DNA methylation positive scores detected anytime in the follow-up period, 64 were obtained from patients who ultimately had recurrence (90%, true positive prediction rate, TPR), whereas 182 out of 221 samples with negative scores correlated with no recurrence (82%, true negative prediction rate, TNR) (FIG. 4C). The results demonstrate that the three-marker model can predict late recurrence with remarkably high probability, when compared to cytology (7%) or cystoscopy (4%). On the other hand, 47% of patients (16 out of 34 cases) whose samples showed positive DNA methylation scores for the first time developed recurrence later. Samples from five of these 16 patients consistently displayed positive scores, samples from two showed subsequent fluctuating results; and samples from the remaining nine had only one collection point prior to recurrence. In addition, 4 out of 56 control cases with no recurrence had a positive score test history (7%). These data highlight the importance of the score history in the accurate interpretation of the results from the three-marker model. Taken together, the results indicate that, unlike cytology, DNA methylation markers detected in urine sediments collected in early follow-up visits can reliably predict recurrence with a low false-positive prediction rate (7%).

Example 5

Exemplary Methods

A. Patients and Sample Collection.

The study population includes patients under surveillance for tumor recurrence TURBT for superficial NMIBC. Urine samples were obtained from 90 such NMIBC patients at each available clinical follow-up visit. Patient's age ranged from 41 to 96 years old, with a median age of 69. Urine collection at follow-up visits was performed at the Department of Urology, Keck School of Medicine of University of Southern California (USC) from 1991 to 2010 according to the institutional guidelines of the USC Norris Comprehensive Cancer Center. If deemed necessary due to clinical suspicion of recurrence, adjuvant intravesical therapy after tumor resection with chemo (Mitomycin) or immunotherapy (Bacile Calmette-Guerin; BCG) was administered at the Department of Urology, Keck School of Medicine of USC at routine intervals. A total of 368 samples were collected under patient informed consent at different follow-up visits over a period ranging from five to 89 months, depending on the patient. The timeline of urine sample collection is presented in FIG. 1A. The clinicopathological characteristics of all the samples are summarized in Table 1. Tumor recurrence was confirmed by any of the following: biopsy or histologically proven bladder tumor, severe atypia or papillary lesions in cytology or cystoscopy, or any concurrent suspicious criterion after a previous surgery. Over the collection period, 34 patients had tumor recurrence, while 56 patients were not diagnosed with recurrence through the last follow-up visit. The clinical characteristics of 34 recurrent samples are summarized in Table 2. Out of the 34 patients with recurrence, 31 provided a urine sample at the time of diagnosis. Approval for research on human subjects was obtained from the USC Norris Comprehensive Cancer Center review boards. Tumors were diagnosed according to the criteria of the American Joint Committee on cancer (Edge, Byrd et al. 2010) and staging and grading was based on the TNM classification of the International Union Against Cancer (Sobin, Gospodarowicz et al. 2009).

B. DNA Extraction from Urine Sediments and DNA Methylation Analysis by Pyrosequencing.

Urine samples (~50 ml) were centrifuged for 10 min at 1500 g and DNA extraction from urine sediments was performed as previously reported (Friedrich, Weisenberger et al. 2004). DNA was bisulfite-converted using EZ DNA Methylation Kit (Zymo Research, Irvine, Calif., USA) according to the manufacturer's instructions. Six DNA methylation markers were selected from our previous study (Wolff, Chihara et al. 2010); the regions of interest were PCR amplified using biotin-labeled primers (table 4) and analyzed by pyrosequencing, a high throughput and quantitative tool for DNA sequence detection. The percentage of methylated cytosines divided by the sum of methylated and unmethylated cytosines was measured using PSQ HS96 (Qiagen, Valencia, Calif., USA) as previously described (Wolff, Byun et al. 2010).

C. Statistical Analysis.

ROC curves summarize the accuracy of our markers in DNA urine sediment from 87 independent samples, selected at the time of the last follow up visit for non-recurrent patients (n=56), or at the time of first recurrence for the patients with recurrence (n=31). A subset of 83 patients with complete data on all markers was used to build a multivariable predictor model. We used stepwise logistic regression, selecting variables to add or subtract based on the Akaike Information Criterion. Sensitivity and specificity were estimated using five-fold cross-validation, repeating the model selection for each subdivision of the data. The final model was then evaluated on the remaining samples from our data set. Control samples included visits prior to the last follow-up visit where the patient was not diagnosed with bladder cancer; case samples included recurrences occurring after the first recurrence and samples at the initial clinic visit when the patient presented with bladder cancer.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.

Babjuk, M., W. Oosterlinck, R. Sylvester, E. Kaasinen, A. Bohle, J. Palou-Redorta, M. Roupret and E. A. o. U. (EAU) (2011). "EAU guidelines on non-muscle-invasive urothelial carcinoma of the bladder, the 2011 update." Eur Urol 59(6): 997-1008.

Brems-Eskildsen, A. S., K. Zieger, H. Toldbod, C. Holcomb, R. Higuchi, F. Mansilla, P. P. Munksgaard, M. Borre, T. F. ørntoft and L. Dyrskjot (2010). "Prediction and diagnosis of bladder cancer recurrence based on urinary content of hTERT, SENP1, PPP1CA, and MCMS transcripts." BMC Cancer 10: 646.

Chan, M. W., L. W. Chan, N. L. Tang, J. H. Tong, K. W. Lo, T. L. Lee, H. Y. Cheung, W. S. Wong, P. S. Chan, F. M. Lai and K. F. To (2002). "Hypermethylation of multiple genes in tumor tissues and voided urine in urinary bladder cancer patients." Clin Cancer Res 8(2): 464-470.

Chung, W., J. Bondaruk, J. Jelinek, Y. Lotan, S. Liang, B. Czerniak and J. P. Issa (2011). "Detection of bladder cancer using novel DNA methylation biomarkers in urine sediments." Cancer Epidemiol Biomarkers Prev 20(7): 1483-1491.

Costa, V. L., R. Henrique, S. A. Danielsen, S. Duarte-Pereira, M. Eknaes, R. I. Skotheim, A. Rodrigues, J. S. Magalhães, J. Oliveira, R. A. Lothe, M. R. Teixeira, C. Jerónimo and G. E. Lind (2010). "Three epigenetic biomarkers, GDF15, TMEFF2, and VIM, accurately predict bladder cancer from DNA-based analyses of urine samples." Clin Cancer Res 16(23): 5842-5851.

De Carvalho, D. D., S. Sharma, J. S. You, S. F. Su, P. C. Taberlay, T. K. Kelly, X. Yang, G. Liang and P. A. Jones (2012). "DNA methylation screening identifies driver epigenetic events of cancer cell survival." Cancer Cell 21(5): 655-667.

Dulaimi, E., R. G. Uzzo, R. E. Greenberg, T. Al-Saleem and P. Cairns (2004). "Detection of bladder cancer in urine by a tumor suppressor gene hypermethylation panel." Clin Cancer Res 10(6): 1887-1893.

Edge, S. B., D. R. Byrd, C. C. Compton, A. G. Fritz, F. L. Greene, A. Trotti, S. Edge, D. Byrd, C. Compton, A. Fritz, F. Greene and A. Trotti (2010). AJCC Cancer Staging Manual, 7th edition. New York, Springer-Verlag.

Friedrich, M. G., S. Chandrasoma, K. D. Siegmund, D. J. Weisenberger, J. C. Cheng, M. I. Toma, H. Huland, P. A.

Jones and G. Liang (2005). "Prognostic relevance of methylation markers in patients with non-muscle invasive bladder carcinoma." Eur J Cancer 41(17): 2769-2778.

Friedrich, M. G., D. J. Weisenberger, J. C. Cheng, S. Chandrasoma, K. D. Siegmund, M. L. Gonzalgo, M. I. Toma, H. Huland, C. Yoo, Y. C. Tsai, P. W. Nichols, B. H. Bochner, P. A. Jones and G. Liang (2004). "Detection of methylated apoptosis-associated genes in urine sediments of bladder cancer patients." Clin Cancer Res 10(22): 7457-7465.

Hogue, M. O., S. Begum, O. Topaloglu, A. Chatterjee, E. Rosenbaum, W. Van Criekinge, W. H. Westra, M. Schoenberg, M. Zahurak, S. N. Goodman and D. Sidransky (2006). "Quantitation of promoter methylation of multiple genes in urine DNA and bladder cancer detection." J Natl Cancer Inst 98(14): 996-1004.

Jones, P. A. (1999). "The DNA methylation paradox." Trends Genet 15(1): 34-37.

Jones, P. A. (2002). "DNA methylation and cancer." Oncogene 21(35): 5358-5360.

Jones, P. A. (2012). "Functions of DNA methylation: islands, start sites, gene bodies and beyond." Nat Rev Genet 13(7): 484-492.

Jones, P. A. and S. B. Baylin (2002). "The fundamental role of epigenetic events in cancer." Nat Rev Genet 3(6): 415-428.

Jürgens, B., B. J. Schmitz-Drager and W. A. Schulz (1996). "Hypomethylation of L1 LINE sequences prevailing in human urothelial carcinoma." Cancer Res 56(24): 5698-5703.

Kandimalla, R., A. A. van Tilborg, L. C. Kompier, D. J. Stumpel, R. W. Stam, C. H. Bangma and E. C. Zwarthoff (2012). "Genome-wide analysis of CpG island methylation in bladder cancer identified TBX2, TBX3, GATA2, and ZIC4 as pTa-specific prognostic markers." Eur Urol 61(6): 1245-1256.

Kim, W. J. and Y. J. Kim (2009). "Epigenetic biomarkers in urothelial bladder cancer." Expert Rev Mol Diagn 9(3): 259-269.

Kim, Y. K. and W. J. Kim (2009). "Epigenetic markers as promising prognosticators for bladder cancer." Int J Urol 16(1): 17-22.

Kompier, L. C., I. Lurkin, M. N. van der Aa, B. W. van Rhijn, T. H. van der Kwast and E. C. Zwarthoff (2010). "FGFR3, HRAS, KRAS, NRAS and PIK3CA mutations in bladder cancer and their potential as biomarkers for surveillance and therapy." PLoS One 5(11): e13821.

Laird, P. W. (2003). "The power and the promise of DNA methylation markers." Nat Rev Cancer 3(4): 253-266.

Lin, H. H., H. L. Ke, S. P. Huang, W. J. Wu, Y. K. Chen and L. L. Chang (2010). "Increase sensitivity in detecting superficial, low grade bladder cancer by combination analysis of hypermethylation of E-cadherin, p16, p14, RASSF1A genes in urine." Urol Oncol 28(6): 597-602.

Lintula, S. and K. Hotakainen (2010). "Developing biomarkers for improved diagnosis and treatment outcome monitoring of bladder cancer." Expert Opin Biol Ther 10(8): 1169-1180.

Millan-Rodriguez, F., G. Chéchile-Toniolo, J. Salvador-Bayarri, J. Palou, F.

Algaba and J. Vicente-Rodriguez (2000). "Primary superficial bladder cancer risk groups according to progression, mortality and recurrence." J Urol 164(3 Pt 1): 680-684.

Morgan, T. M. and P. E. Clark (2010). "Bladder cancer." Curr Opin Oncol 22(3): 242-249.

Negraes, P. D., F. P. Favaro, J. L. Camargo, M. L. Oliveira, J. Goldberg, C. A. Rainho and D. M. Salvadori (2008). "DNA methylation patterns in bladder cancer and washing cell sediments: a perspective for tumor recurrence detection." BMC Cancer 8: 238.

Parker, J. and P. E. Spiess (2011). "Current and emerging bladder cancer urinary biomarkers." ScientificWorldJournal 11: 1103-1112.

Reinert, T. (2012). "Methylation Markers for Urine-Based Detection of Bladder Cancer: The Next Generation of Urinary Markers for Diagnosis and Surveillance of Bladder Cancer." Adv Urol 2012: 503271.

Reinert, T., C. Modin, F. M. Castano, P. Lamy, T. K. Wojdacz, L. L. Hansen, C. Wiuf, M. Borre, L. Dyrskjot and T. F. Orntoft (2011). "Comprehensive genome methylation analysis in bladder cancer: identification and validation of novel methylated genes and application of these as urinary tumor markers." Clin Cancer Res 17(17): 5582-5592.

Roupret, M., V. Hupertan, D. R. Yates, E. Comperat, J. W. Catto, M. Meuth, A. Lackmichi, S. Ricci, R. Lacave, B. Gattegno, F. Richard, F. C. Hamdy and O. Cussenot (2008). "A comparison of the performance of microsatellite and methylation urine analysis for predicting the recurrence of urothelial cell carcinoma, and definition of a set of markers by Bayesian network analysis." BJU Int 101(11): 1448-1453.

Seifert, H. H., V. Schmiemann, M. Mueller, M. Kazimirek, F. Onofre, A. Neuhausen, A. R. Florl, R. Ackermann, A. Boecking, W. A. Schulz and H. J. Grote (2007). "In situ detection of global DNA hypomethylation in exfoliative urine cytology of patients with suspected bladder cancer." Exp Mol Pathol 82(3): 292-297.

Shelley, M. D., M. D. Mason and H. Kynaston (2010). "Intravesical therapy for superficial bladder cancer: a systematic review of randomised trials and meta-analyses." Cancer Treat Rev 36(3): 195-205.

Siegel, R., E. Ward, O. Brawley and A. Jemal (2011). "Cancer statistics, 2011: the impact of eliminating socioeconomic and racial disparities on premature cancer deaths." CA Cancer J Clin 61(4): 212-236.

Sobin, L. H., M. K. Gospodarowicz and W. Christian (2009). TNM Classification of Malignant Tumours, 7th Edition, Wiley-Blackwell.

Steiner, G., M. P. Schoenberg, J. F. Linn, L. Mao and D. Sidransky (1997). "Detection of bladder cancer recurrence by microsatellite analysis of urine." Nat Med 3(6): 621-624.

Sturgeon, C. M., M. J. Duffy, B. R. Hofmann, R. Lamerz, H. A. Fritsche, K. Gaarenstroom, J. Bonfrer, T. H. Ecke, H. B. Grossman, P. Hayes, R. T. Hoffmann, S. P. Lerner, F. Lithe, J. Louhimo, I. Sawczuk, K. Taketa, E. P. Diamandis and N. A. o. C. Biochemistry (2010). "National Academy of Clinical Biochemistry Laboratory Medicine Practice Guidelines for use of tumor markers in liver, bladder, cervical, and gastric cancers." Clin Chem 56(6): el-48.

Sylvester, R. J., A. P. van der Meij den, W. Oosterlinck, J. A. Witjes, C. Bouffioux, L. Denis, D. W. Newling and K. Kurth (2006). "Predicting recurrence and progression in individual patients with stage Ta T1 bladder cancer using EORTC risk tables: a combined analysis of 2596 patients from seven EORTC trials." Eur Urol 49(3): 466-465; discussion 475-467.

Tada, Y., M. Wada, K. Taguchi, Y. Mochida, N. Kinugawa, M. Tsuneyoshi, S. Naito and M. Kuwano (2002). "The association of death-associated protein kinase hypermethylation with early recurrence in superficial bladder cancers." Cancer Res 62(14): 4048-4053.

Tilki, D., M. Burger, G. Dalbagni, H. B. Grossman, O. W. Hakenberg, J. Palou, O. Reich, M. Rouprêt, S. F. Shariat and A. R. Zlotta (2011). "Urine markers for detection and surveillance of non-muscle-invasive bladder cancer." Eur Urol 60(3): 484-492.

Wolff, E. M., H. M. Byun, H. F. Han, S. Sharma, P. W. Nichols, K. D. Siegmund, A. S. Yang, P. A. Jones and G. Liang (2010). "Hypomethylation of a LINE-1 promoter activates an alternate transcript of the MET oncogene in bladders with cancer." PLoS Genet 6(4): e1000917.

Wolff, E. M., Y. Chihara, F. Pan, D. J. Weisenberger, K. D. Siegmund, K. Sugano, K. Kawashima, P. W. Laird, P. A. Jones and G. Liang (2010). "Unique DNA methylation patterns distinguish noninvasive and invasive urothelial cancers and establish an epigenetic field defect in premalignant tissue." Cancer Res 70(20): 8169-8178.

Wolff, E. M., G. Liang and P. A. Jones (2005). "Mechanisms of Disease: genetic and epigenetic alterations that drive bladder cancer." Nat Clin Pract Urol 2(10): 502-510.

Zhao, Y., S. Guo, J. Sun, Z. Huang, T. Zhu, H. Zhang, J. Gu, Y. He, W. Wang, K. Ma, J. Wang and J. Yu (2012). "Methylcap-seq reveals novel DNA methylation markers for the diagnosis and recurrence prediction of bladder cancer in a Chinese population." PLoS One 7(4): e35175.

Zuiverloon, T. C., W. Beukers, K. A. van der Keur, J. R. Munoz, C. H. Bangma, H. F. Lingsma, M. J. Eijkemans, J. P. Schouten and E. C. Zwarthoff (2012). "A methylation assay for the detection of non-muscle-invasive bladder cancer (NMIBC) recurrences in voided urine." BJU Int 109(6): 941-948.

Zuiverloon, T. C., M. N. van der Aa, T. H. van der Kwast, E. W. Steyerberg, H. F. Lingsma, C. H. Bangma and E. C. Zwarthoff (2010). "Fibroblast growth factor receptor 3 mutation analysis on voided urine for surveillance of patients with low-grade non-muscle-invasive bladder cancer." Clin Cancer Res 16(11): 3011-3018.

TABLE 1

The Clinicopathological Characteristics of 90 TURBT Patients

| Characteristic | No recurrence N = 56 | Recurrence N = 34 |
|---|---|---|
| Age - yr | | |
| Median | 71 | 69 |
| Range | 42-96 | 41-87 |
| Sex - no. (%) | | |
| Male | 48 (86) | 27 (79) |
| Female | 8 (14) | 7 (21) |
| Histology TCC - no. (%) | 57 (100) | 34 (100) |
| Number of tumors - no. (%) | | |
| Unifoci | 19 (34) | 18 (53) |
| Multifoci | 16 (29) | 12 (35) |
| Missing | 21 (37) | 4 (12) |
| T Stage - no. (%) | | |
| Tis | 2 (4) | 1 (3) |
| Ta | 37 (66) | 19 (56) |
| T1 | 17 (30) | 14 (41) |
| Tumor grade[§] - no. (%) | | |
| Low | 26 (46) | 17 (50) |
| High | 30 (54) | 17 (50) |
| Concomitant CIS - no. (%) | 11 (20) | 7 (21) |
| Treatment - no. (%) | | |
| Adjuvant BCG | 36 (64) | 20 (59) |
| Adjuvant chemotherapy instillation | 11 (19) | 12 (35) |
| Follow-up time since TURBT -yr | 55 (0.6-9.7) | 4.7 (0.4-26) |

TABLE 1-continued

The Clinicopathological Characteristics of 90 TURBT Patients

| Characteristic | No recurrence N = 56 | Recurrence N = 34 |
|---|---|---|
| Study follow-up time - yr | 3.5 (0.4-7.1) | 3.6 (0.5-7.4) |
| Total urines analyzed - no. | 208 | 160 |
| Urines analyzed patient - no. | | |
| Mean (±SD) | 3.7 ± 1.8 | 4.7 ± 2.1 |
| Range | 2-9 | 2-10 |

[§]Grade 1 and 2 are low grade. Grade 3 and more are high grade.
TCC: transitional cell carcinoma;
TURBT: transurethral resection of bladder tumor;
CIS: carcinoma in situ;
BCG: *Bacillus* Calmette-Guerin

TABLE 2

The Clinical Characteristics of 34 Recurrence Bladder Cancer Patients

| Characteristic | Baseline N = 34 | Recurrence |
|---|---|---|
| Histology TCC - no. (%) | 34 (100) | 30 (88) |
| Number of tumors - no. (%) | | |
| Unifoci | 18 (53) | 19 (56) |
| Multifoci | 12 (35) | 12 (35) |
| Missing | 4 (12) | 3 (9) |
| T Stage - no. (%) | | |
| Tis | 1 (3) | 4 (12) |
| Ta | 19 (56) | 20 (59) |
| T1 | 14 (41) | 2 (6) |
| T2 | 0 | 1 (3) |
| Missing | 0 | 7 (20) |
| Tumor grade[§] - no. (%) | | |
| Low | 17 (50) | 16 (47) |
| High | 17 (50) | 13 (38) |
| Missing | 0 | 5 (15) |
| Treatment - no. (%) | | |
| Adjuvant BCG | 20 (59) | 15 (44) |
| Adjuvant chemotherapy instillation | 12 (35) | 5 (15) |

| | Baseline | | | Recurrence | | |
|---|---|---|---|---|---|---|
| Patient number | Number of tumors | T Stage | Grade | Number of tumors | T Stage | Grade |
| 4843 | Multifoci | T1 | High | Mulnfoci | TA | High |
| 5137 | Umfoci | Ta | Low | Umfoci | Ta | Low |
| 6664 | Multifoci | T1 | High | Umfoci | Missing | Low |
| 6675 | Umfoci | Ta | Low | Multifoei | Ta | Low |
| 6762 | Missing | Ta | Low | Umfoci | Ta | Low |
| 6804 | Multifoci | T1 | High | Umfoci | Missing | Low |
| 6851 | Umfoci | T1 | High | Umfoci | Ta | Low |
| 7145 | Multifoci | T1 | High | Multifoci | CIS | High |
| 7258 | Umfoci | T1 | High | Umfoci | CIS | High |
| 7346 | Umfoci | Ta | High | Umfoci | Ta | High |
| 7397 | Umfoci | T1 | Low | Multifoci | Ta | Low |
| 7592 | Umfoci | Ta | High | Umfoci | Ta | High |
| 7662 | Missing | Ta | Low | Mulnfoci | Ta | High |
| 7716 | Multifoci | Ta | High | Mulnfoci | Ta | High |
| 7718 | Umfoci | T1 | Low | Umfoci | T1 | High |
| 7728 | Umfoci | T1 | Low | Mulnfoci | Missing | NA |
| 7743 | Umfoci | CIS | CIS | Umfoci | Ta | Low |
| 7774 | Umfoci | Ta | Low | Mulnfoci | Ta | Low |
| 7792 | Multifoci | Ta | Low | Missing | Missing | NA |
| 7809 | Multifoci | Ta | Low | Umfoci | CIS | High |
| 7810 | Umfoci | Ta | Low | Mulufoct | Ta | Low |
| 7817 | Multifoci | Ta | Low | Mulnfoci | Ta | Low |
| 7859 | Multifoci | T1 | High | Umfoci | Ta | High |
| 7873 | Multifoci | Ta | Low | Umfoci | Missing | NA |

TABLE 2-continued

The Clinical Characteristics of 34 Recurrence Bladder Cancer Patients

| 7891 | Missing | T1 | High | Umfoci | CIS | High |
| 7896 | Umfoci | Ta | Low | Umfoci | Ta | Low |
| 8659 | Umfoci | T1 | High | Missing | Missing | NA |
| 8792 | Umfoci | T1 | Hi eh | Umfoci | T2 | High |
| 8928 | Missing | T1 | High | Missing | Missing | NA |
| 9216 | Multifoci | Ta | Low | Umfoci | Ta | Low |
| 9532 | Umfoci | Ta | Low | Umfoci | Ta | Low |
| 9536 | Umfoci | Ta | High | Umfoci | T1 | High |
| 9626 | Umfoci | Ta | Low | Mulnfoci | Ta | Low |
| 9627 | Umfoci | Ta | High | Mulnfoci | Ta | Low |

§Grade 1 and 2 are low grade Grade 3 and more are high grade
TCC: transitional cell carcinoma:
TURBT: transurethral resection of bladder tumor:
CIS: carcinoma in situ:
BCG: *Bacillus* Calmette-Guenn

TABLE 3

DNA Methylation Status in Urine Sediment Samples of TURBT Patients at the Time of First Recurrence and the Last Follow-up Visit of No Recurrence Patients

| Methylated gene | No Recurrence (n = 56) | Recurrence (n = 31) | P value |
|---|---|---|---|
| | DNA Methylation % (mean ± SD) | | |
| HOXA9 | 11.4 ± 9.6 | 38.4 ± 19.6 | $3.16 \times 10^{-13}$ |
| SOX1 | 10.8 ± 5.4 | 35.5 ± 16.9 | $3.97 \times 10^{-16}$ |
| NPY | 9.4# ± 5.7 | 32.1 ± 17.9 | $2.25 \times 10^{-13}$ |
| IRAK3 | 5.8 ± 4.0 | 20.3 ± 17.7 | $7.27 \times 10^{-8}$ |
| TJP2 | 19.0 ± 12.3 | 52.7 ± 23.0 | $7.87 \times 10^{-14}$ |
| L1-MET | 74.2^ ± 13.4 | 44.7* ± 14 7 | $2.01 \times 10^{-14}$ | n = 55;
^n = 55;
*n = 29
P value was calculated by the paired t-test.

TABLE 4

Primer Sequence Used in Pyrosequencing

| Primer Name | Sequence | Amplicon Size |
|---|---|---|
| HOXA9 | | 91 |
| sense | 5' ATGAAATTTGTAGTTTTATAATTTT (SEQ ID NO: 1) | |
| anti-sence | 5' Biotin-ATTACCCAAAACCCCAAT AATAAC (SEQ ID NO: 2) | |
| sequen-cing | 5' GTTTTATAATTTT (SEQ ID NO: 3) | |
| SOX1 | | 109 |
| sense | 5' GGTATTTGGGATTAGTATATGTTTAG (SEQ ID NO: 4) | |
| anti-sence | 5' Biotin-CTATCTCCTTCCTCCTAC (SEQ ID NO: 5) | |
| sequen-cing | 5' TTAGTATATGTTTAG (SEQ ID NO: 6) | |
| NPY | | 106 |
| sense | 5' GGGTTGTTTTTATTTTTGGTAGGATT AGA (SEQ ID NO: 7) | |
| anti-sence | 5' Biotin-CACCAAAACCCAAATATCTA (SEQ ID NO: 8) | |
| sequen-cing | 5' AGGAAAGTAGGGAT (SEQ ID NO: 9) | |
| IRAK3 | | 136 |
| sense | 5' GGAGTTTTGAGTTTTGGGTTTT (SEQ ID NO: 10) | |
| anti-sence | 5' Biotin-CCTAACCAAACCTAAAAATT ACC (SEQ ID NO: 11) | |
| sequen-cing | 5' AGGTGTGAAGGGG (SEQ ID NO: 12) | |
| TJP2 | | 84 |
| sense | 5' GGTTTTTAGATAGGATTTAAAATTTT GAG (SEQ ID NO: 13) | |
| anti-sence | 5' Biotin-CAAAACCTCACACAAACAAC TTC (SEQ ID NO: 14) | |
| sequen-cing | 5' AGGTTTTTTTAGTT (SEQ ID NO: 15) | |
| L1-MET | | 294 |
| sense | 5' GTGTTTTTTAAGTGAGGTAATGTT (SEQ ID NO: 16) | |
| anti-sence | 5' Biotin-ATC CAACCACTACAAACTAC (SEQ ID NO: 17) | |
| sequen-cing | 5' GTTGGGAGTTGTAGAT (SEQ ID NO: 18) | |

TABLE 5

Association between the Score from the Three-Marker Signature and the Bladder Tumor Pathological Characteristics of 90 TURBT Patients

| Primary Tumor | No Recurrence (N = 56) | Recurrence (N = 34) |
|---|---|---|
| Tumor number | N, DNA methylation score (mean ± SD) | |
| unifoci | 18, -4.0 ± 2.5 | 18, 5.7 ± 8.3 |
| multifoci | 17, -4.6 ± 2.5 | 11, 5.0 ± 4.1 |
| Tumor stage | | |
| Tis | 2, -5.2 ± 1.4 | 1, 0.3 |
| Ta | 37, -4.7 ± 2.4 | 18, 4.0 ± 4.6 |
| T1 | 17, -4.2 ± 2.7 | 14, 7.2 ± 8.2 |
| Tumor grade | | |
| Low | 26, -4.1 ± 2.7 | 16, 2.7 ± 3.1 |*
| High | 30, -5.0 ± 2.1 | 17, 7.5 ± 7.8 |
| | -4.5 ± 2.4 | 5.2 ± 6.4 *** |

TABLE 5-continued

Association between the Score from the Three-Marker Signature and the Bladder Tumor Pathological Characteristics of 90 TURBT Patients

| | DNA methylation score | | |
|---|---|---|---|
| Primary Tumor | Negative | Positive | Missing |
| Tumor number | | n (%) | |
| unifoci (N = 37) | 19 (51) | 14 (38) | 4 (11) |
| multifoci (N = 29) | 16 (55) | 12 (41) | 1 (4) |
| Tumor stage | | | |
| Tis (N = 3) | 2 (67) | 1 (33) | |
| Ta (N = 57) | 38 (67) | 16 (28) | 3 (5) |
| T1 (N = 31) | 15 (48) | 13 (42) | 3 (10) |
| Tumor grade | | | |
| Low (N = 44) | 27 (61) | 14 (32) | 3 (7) |
| High (N = 47) | 28 (60) | 16 (34) | 3 (6) |

Paired t-test was performed.
* $p < 0.05$; *** $p < 0.001$.

---

What is claimed is:

1. A method for providing treatment for bladder cancer or bladder cancer recurrence in a human subject comprising:
   providing a test sample from the subject, wherein the test sample is urine;
   measuring a DNA methylation level of at least a portion of polynucleotides consisting of SOX1, IRAK3, and L1-MET, and one or more of HOXA9, NPY1 and ZO2 polynucleotides in the test sample;
   comparing the DNA methylation level of the polynucleotides in the test sample to a reference DNA methylation profile based on the DNA methylation levels of the polynucleotides in a control group, members of which had bladder cancer;
   based on the comparison, determining at least one of: (1) whether bladder cancer has recurred; (2) whether there is likelihood that the bladder cancer will recur; and (3) whether the patient has bladder cancer; and
   providing a cancer treatment to the subject, wherein the cancer treatment is tumor resection, chemotherapy and/or immunotherapy.

2. The method of claim 1, wherein the polynucleotides further comprise HOXA9.

3. The method of claim 1, wherein the polynucleotides include at least one hypomethylated polynucleotide and at least one hypermethylated polynucleotide.

4. The method of claim 1, further comprising: extracting DNA from the test sample, bisulfite conversion, and PCR amplification.

5. The method of claim 1, wherein DNA methylation levels is a percentage of methylated cytosines, defined as a number of methylated cytosines divided by the sum of methylated and unmethylated cytosines.

6. The method of claim 1, wherein the urine comprises urine sediment.

* * * * *